(12) United States Patent
Cable et al.

(10) Patent No.: US 9,008,758 B2
(45) Date of Patent: *Apr. 14, 2015

(54) MULTI-MODE INTERNAL IMAGING

(75) Inventors: Michael D. Cable, Danville, CA (US);
Bradley W. Rice, Danville, CA (US);
David Nilson, Walnut Creek, CA (US)

(73) Assignee: Xenogen Corporation, Alameda, CA (US)

( * ) Notice: Subject to any disclaimer, the term of this patent is extended or adjusted under 35 U.S.C. 154(b) by 40 days.

This patent is subject to a terminal disclaimer.

(21) Appl. No.: 12/978,270

(22) Filed: Dec. 23, 2010

(65) Prior Publication Data

US 2011/0092813 A1 Apr. 21, 2011

Related U.S. Application Data

(63) Continuation of application No. 11/485,920, filed on Jul. 12, 2006, now Pat. No. 7,881,773, which is a continuation of application No. 10/881,707, filed on Jun. 29, 2004, now Pat. No. 7,190,991.

(60) Provisional application No. 60/484,186, filed on Jul. 1, 2003.

(51) Int. Cl.
*A61B 5/05* (2006.01)
*G01N 21/76* (2006.01)
(Continued)

(52) U.S. Cl.
CPC .............. *G01N 21/76* (2013.01); *A61B 5/0059* (2013.01); *A61B 5/0077* (2013.01); *A61B 6/032* (2013.01);
(Continued)

(58) Field of Classification Search
USPC ......... 600/407, 411, 415, 427, 431, 436, 476; 5/601; 128/203.12; 250/363.02–363.04; 1/407, 411, 415, 1/427, 431, 436, 476
See application file for complete search history.

(56) References Cited

U.S. PATENT DOCUMENTS 3,944,207 A 3/1976 Bains
5,013,018 A * 5/1991 Sicek et al. ................ 5/601
(Continued)

FOREIGN PATENT DOCUMENTS

WO WO01/63247 8/2001
WO WO03/006966 1/2003
WO WO 2004/008123 1/2004

OTHER PUBLICATIONS

Black, D., "A Modular Approach to Robotic Automation of DOE Applications", First Posted Online Apr. 23, 2003, ARM Automation Inc., pp. 1-10.*

(Continued)

*Primary Examiner* — Christopher Cook
(74) *Attorney, Agent, or Firm* — Fish & Richardson P.C.

(57) ABSTRACT

The invention described herein provides systems and methods for multi-modal imaging with light and a second form of imaging. Light imaging involves the capture of low intensity light from a light-emitting object. A camera obtains a two-dimensional spatial distribution of the light emitted from the surface of the subject. Software operated by a computer in communication with the camera may then convert two-dimensional spatial distribution data from one or more images into a three-dimensional spatial representation. The second imaging mode may include any imaging technique that compliments light imaging. Examples include magnetic resonance imaging (MRI) and computer topography (CT). An object handling system moves the object to be imaged between the light imaging system and the second imaging system, and is configured to interface with each system.

7 Claims, 16 Drawing Sheets

(51) Int. Cl.

| | |
|---|---|
| *A61B 5/00* | (2006.01) |
| *A61B 6/03* | (2006.01) |
| *A61B 6/00* | (2006.01) |
| *A61B 8/00* | (2006.01) |
| *G01N 21/64* | (2006.01) |
| *G01T 1/16* | (2006.01) |
| *G01T 1/164* | (2006.01) |
| *G01T 1/29* | (2006.01) |
| *A61B 8/13* | (2006.01) |
| *G01N 35/00* | (2006.01) |

(52) U.S. Cl.
CPC ............... *A61B 6/5247* (2013.01); *A61B 8/13* (2013.01); *A61B 8/4416* (2013.01); *G01N 21/6456* (2013.01); *G01N 35/0099* (2013.01); *G01T 1/1603* (2013.01); *G01T 1/1648* (2013.01); *G01T 1/2985* (2013.01); *A61B 6/4417* (2013.01)

(56) References Cited

U.S. PATENT DOCUMENTS

| | | | |
|---|---|---|---|
| 5,202,091 | A | 4/1993 | Lisenbee |
| 5,319,209 | A | 6/1994 | Miyakawa et al. |
| 5,414,258 | A | 5/1995 | Liang |
| 5,525,905 | A | 6/1996 | Mohapatra et al. |
| 5,636,299 | A | 6/1997 | Bueno et al. |
| 5,637,874 | A | 6/1997 | Honzawa et al. |
| 5,650,135 | A | 7/1997 | Contag et al. |
| 5,672,881 | A | 9/1997 | Striepeke et al. |
| 5,705,807 | A | 1/1998 | Throngnumchai et al. |
| 5,738,101 | A | 4/1998 | Sappey |
| 5,840,572 | A | 11/1998 | Copeland et al. |
| 5,851,182 | A | 12/1998 | Sahadevan |
| 5,867,250 | A | 2/1999 | Baron |
| 5,903,001 | A | 5/1999 | Tsai |
| 5,917,882 | A | 6/1999 | Khutoryansky et al. |
| 5,960,098 | A | 9/1999 | Tao |
| 5,970,164 | A | 10/1999 | Bamberger et al. |
| 5,999,167 | A | 12/1999 | Marsh et al. |
| 6,032,070 | A | 2/2000 | Flock et al. |
| 6,066,857 | A | 5/2000 | Fantone et al. |
| 6,101,236 | A | 8/2000 | Wang et al. |
| 6,201,889 | B1* | 3/2001 | Vannah ............... 382/131 |
| 6,205,347 | B1* | 3/2001 | Morgan et al. ............ 600/407 |
| 6,217,847 | B1 | 4/2001 | Contag et al. |
| 6,241,668 | B1 | 6/2001 | Herzog |
| 6,242,743 | B1 | 6/2001 | DeVito et al. |
| 6,246,610 | B1 | 6/2001 | Han et al. |
| 6,264,610 | B1 | 7/2001 | Zhu |
| 6,271,972 | B1 | 8/2001 | Kedar et al. |
| 6,321,111 | B1 | 11/2001 | Perelman et al. |
| 6,364,829 | B1 | 4/2002 | Fulghum |
| 6,370,413 | B1 | 4/2002 | Alvarez et al. |
| 6,377,369 | B1 | 4/2002 | Preston |
| 6,442,777 | B1 | 9/2002 | Pauli |
| 6,475,161 | B2 | 11/2002 | Teicher et al. |
| 6,490,476 | B1 | 12/2002 | Townsend et al. |
| 6,505,063 | B2 | 1/2003 | Van Den Brink et al. |
| 6,535,821 | B2 | 3/2003 | Wang et al. |
| 6,615,063 | B1 | 9/2003 | Ntziachristos et al. |
| 6,631,284 | B2 | 10/2003 | Nutt et al. |
| 6,674,449 | B1 | 1/2004 | Banks et al. |
| 6,775,567 | B2 | 8/2004 | Cable et al. |
| 7,190,991 | B2* | 3/2007 | Cable et al. ............ 600/407 |
| 7,813,782 | B2* | 10/2010 | Cable et al. ............ 600/407 |
| 7,881,773 | B2* | 2/2011 | Cable et al. ............ 600/427 |
| 2003/0002028 | A1* | 1/2003 | Rice et al. ............ 356/39 |
| 2003/0036860 | A1 | 2/2003 | Rice et al. |
| 2003/0076925 | A1* | 4/2003 | DeSilets et al. ............ 378/63 |
| 2003/0086535 | A1 | 5/2003 | Teppaz et al. |
| 2004/0024303 | A1 | 2/2004 | Banks et al. |
| 2004/0131234 | A1 | 7/2004 | Long et al. |
| 2004/0249260 | A1 | 12/2004 | Wang et al. |
| 2005/0033157 | A1 | 2/2005 | Klein et al. |

OTHER PUBLICATIONS

Wang, Ge; Hoffman, Eric; McLennan, Geoffrey, "Development and Integration of Bioluminescent CT for Molecular and Dynamic Imaging", Bioluminescence Tomography Laboratory, NIH/NIBIB; Mar. 2003-Feb. 2007, 2 web pages, available Jul. 1, 2004.
Mahmood et al., "Near-Infrared Optical Imaging of Protease Activity for Tumor Detection", Radiology, Dec. 1999, p. 866-870.
Weissleder et al., "Shedding Light onto Live Molecular Targets", Nature Medicine, vol. 9, No. 1, Jan. 2003, p. 123-1218.
International Search Report for PCT Application No. PCT/US04/21204, mailed Sep. 27, 2005.
Supplementary Search Report from EP Application No. 04756529.6 dated Mar. 7, 2007.
Magin, "Monitoring pH of Otitis Media Effusion in Chinchillas Using Fluorescence Spectroscopy," IEEE Transactions on Biomedical Engineering, 42 Oct. 1995, No. 10, New York, US.
Austrian Examination Report dated May 4, 2007 in Singapore Application No. 200508123-7.
Chinese Office Action dated Oct. 19, 2007 in Chinese Patent Application No. 200480024375.6.
Canadian Office Action dated Nov. 30, 2007 received in Canadian Patent Application No. 2,530,536.
European Examination Report dated Nov. 21, 2007 in EP Application No. 04 756 529.6.
Chinese Office Action dated Jun. 11, 2008 in Chinese Patent Application No. 200480024375.6.
European Office Action dated Jun. 24, 2008 from European Patent Application No. 04 756 529.6-2305.
Office Action dated Mar. 4, 2009 in U.S. Appl. No. 11/485,920.
Office Action dated Mar. 19, 2009 in U.S. Appl. No. 11/485,923.
Office Action dated Sep. 4, 2009 in U.S. Appl. No. 11/485,923.
Final Office Action dated Sep. 4, 2009 in U.S. Appl. No. 11/485,920.
Office Action dated Jan. 5, 2010 in U.S. Appl. No. 11/485,920.
Black, "A Modular Approach to Robotic Automation of DOE Applications", First Posted Online Apr. 23, 2003, ARM Automation.
Office Action dated Mar. 29, 2010 in U.S. Appl. No. 11/485,923.
Final Office Action dated Jun. 30, 2010 in U.S. Appl. No. 11/485,920.
Notice of Allowance dated Aug. 12, 2010 in U.S. Appl. No. 11/485,923.
Notice of Allowance dated Dec. 6, 2010 in U.S. Appl. No. 11/485,920.

* cited by examiner

MULTI-MODE INTERNAL IMAGING

CROSS-REFERENCE TO RELATED APPLICATIONS

This application claims priority under 35 U.S.C. §120 from and is a continuation of U.S. patent application Ser. No. 11/485,920, filed Jul. 12, 2006, now U.S. Pat. No. 7,881,773, issued Feb. 1, 2011, which in turn claims priority from and is a continuation of U.S. Pat. No. 7,190,991, issued Mar. 13, 2007, which in turn claims priority under 35 U.S.C. §119(e) from U.S. Provisional Patent Application No. 60/484,186, filed Jul. 1, 2003, all of which are entitled "MULTI-MODE INTERNAL IMAGING," and all of which are incorporated by reference herein for all purposes.

TECHNICAL FIELD

The present invention relates to systems and methods for obtaining multiple representations of an internal portion of an object, which is particularly useful in research and imaging applications. In particular, the present invention relates to multi-modal imaging with light and another type of imaging.

Today researchers and imaging practitioners use any one of a number of non-invasive imaging techniques to produce an internal image. These techniques employ X-rays, magnetic resonance imaging (MRI), CAT scans and ultrasound. In other systems, optical imaging is used to produce optical images of an object. For example, bioluminescent imaging is a non-invasive technique for performing in vivo diagnostic studies on animal subjects in the areas of medical research, pathology and drug discovery and development. Bioluminescence is typically produced by cells that have been transfected with a luminescent reporter such as luciferase and can be used as a marker to differentiate a specific tissue type (e.g. a tumor), monitor physiological function, track the distribution of a therapeutic compound administered to the subject, or the progression of a disease. Fluorescence is another optical imaging technology that can be used to track cells or molecules in vivo. This technology has been demonstrated recently using genetically expressed reporters such as green fluorescent protein (GFP) and near infrared (NIR) dyes such as Cy5. Briefly, fluorescence is a molecular phenomenon in which a substance absorbs light of a particular wavelength and emits light of a longer wavelength. The absorption of light is referred to as the "excitation", and the emission of longer wavelengths as the "emission".

Each technique has advantages and disadvantages that make it useful for different imaging applications. Some techniques are well suited to provide spatial or anatomical information for internal parts while others are more suited to provide functional information for an activity of interest within an object being imaged.

Researchers are now finding it desirable to combine the output and strengths of multiple systems. However, the cost of each of these traditional imaging systems has become a barrier to such combination; and becomes even more prohibitive when contemplating multiple techniques at a single site. For instance, an MRI and computer tomography (CT) system can cost millions of dollars. In addition, most traditional imaging systems have practical complications that inhibit implementation in a multiple imaging system environment. MRI systems require that no ferrous metal be near the high power magnet during operation. Positron emission tomography (PET) centers are geographically limited to be close to a particle accelerator device that produces the short-lived radioisotopes used in the technique. Also, transferring an object to be imaged between different imaging systems would be difficult, such as it would be difficult to maintain the spatial accuracy provided by each system without compromise due to object transfer between the systems.

Given the foregoing, new systems for performing multiple modes of imaging would be desirable.

SUMMARY

The present invention provides systems and methods for multi-modal imaging using light and a second form of imaging. Light imaging involves the capture of low intensity light from a light-emitting object. The low intensity light may be emitted from any of a variety of light sources within the object. For example, the light source may correspond to luciferase expressing cells within a living specimen such as a mouse. A camera obtains a two-dimensional spatial distribution of the light emitted from the surface of the subject. Software operated by a computer in communication with the camera may convert two-dimensional (2-D) spatial distribution data from one or more images into a three-dimensional (3-D) spatial representation.

The second imaging mode may include any imaging technique that compliments light imaging. Examples include magnetic resonance imaging (MRI), computer topography (CT), CAT scans; X-rays; ultrasound; nuclear medicine imaging such as positron emission tomography (PET), single photon emission computed tomography (SPECT), cardiovascular imaging, and bone scanning. The second imaging mode may produce spatial information that contributes to a 2-D (pictorial) or 3-D geometric description of the object—or its internal portions.

Software operated by a computer in communication with the light imaging system and the second imaging system may operate to analyze and combine the output provided by each imaging system. For example, light imaging systems are particularly useful to produce functional information relating to an activity of interest within the object. This functional information may be combined with spatial information relating to internal portion of the object as provided by the second imaging system.

In one aspect, the present invention relates to a system for providing multiple modes of imaging data for an internal portion of an object. The system includes a light imaging system that provides light data related to light emitted from a light source located inside the object. The light imaging system includes a) an imaging chamber comprising an interior cavity and b) a camera configured to capture light data from the object while the object is in the interior cavity. The system also includes a second imaging system configured to provide imaging data for the internal portion of the object and having a receiving area that allows the internal portion to be imaged while the object is in the receiving area. The system additionally includes at least one processing device in logical communication with the light imaging system and in logical communication with the second imaging system.

The system comprises a portable stage that supports the object during positioning, and may also include a manipulator configured to move the portable stage between the interior cavity of the imaging chamber and the ambient area surrounding the imaging chamber. The system can also include a light seal configured to interface with a light seal on an exterior wall of the imaging chamber and provide a substantially light tight seal between the interior cavity of the light imaging system and the space outside the imaging chamber while the portable stage is within the interior cavity of the imaging chamber.

In yet another aspect, the present invention pertains to an imaging system for obtaining a representation of a light source located inside a sample. The imaging system comprises an imaging chamber includes a) an interior cavity, b) a camera mount configured to position a camera to capture light data from the object while the object is in the interior cavity, and c) a light seal on an exterior wall of the imaging chamber. The imaging system also comprises an object handling system including a) a portable stage that supports the object, b) a manipulator configured to move the portable stage between the interior cavity of the imaging chamber and the ambient area surrounding the imaging chamber; and c) a light seal associated with the manipulator or portable stage and configured to interface with the light seal on the exterior wall of the imaging chamber and provide a substantially light tight seal between the interior cavity of the light imaging system and the space outside the imaging chamber while the portable stage is within the interior cavity of the imaging chamber.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

1. Overview

Figure 1A:
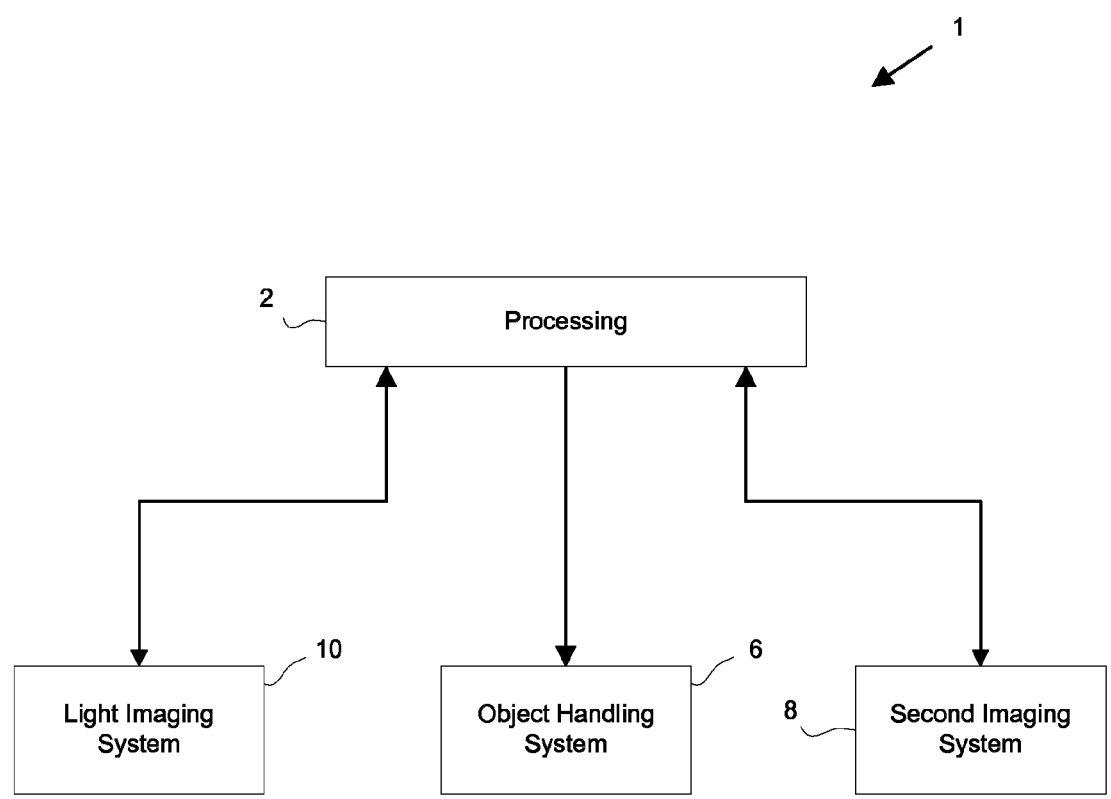
FIG. 1A illustrates a system for providing multiple modes of imaging data for an internal portion of an object in accordance with one embodiment of the present invention.

FIG. 1A illustrates a simplified system 1 for providing multiple modes of imaging data for an internal portion of an object in accordance with one embodiment of the present invention. System 1 comprises a light imaging system 10, a second imaging system 8, an object handling system 6, and at least one processor 2. The object handling system 6 transfers an object (or sample) being imaged between an interior cavity of the light imaging system and a receiving area of the second imaging system. While the present invention will now be primarily described with respect to combining data from two imaging systems, system 1 may include more than two systems and the illustrative embodiment is not meant to limit the number of systems combined.

Light imaging using system 10 involves the capture of low intensity light—often on the order of about $10^3$ to about $10^{10}$ photons/second/centimeter squared/steradian—from a light-emitting object. The low intensity light may be emitted from any of a variety of light sources within the object. For example, the light source may correspond to luciferase expressing cells within a living specimen such as a mouse. The light source indicates portions of the sample, such as traced molecules in a particular portion of a living specimen, where an activity of interest may be taking place.

Light imaging system 10 employs a camera to obtain a two-dimensional (2-D) spatial distribution of light emitted from the surface of an object. To provide details of the light source inside an object (rather than a surface emission), processor 2 operates on stored instructions to construct a three-dimensional (3-D) representation of a light source located inside a sample. This involves converting surface light emission data into light data internal to the sample surface. Parameters for an internal 3-D light source representation may include details related to the source emission strength, 3-D position and geometry.

The second imaging system 8 employs any one of a variety of imaging modes. Exemplary imaging systems include: magnetic resonance imaging (MRI) systems; computer tomography (CT) systems; CAT scan systems; X-ray systems; ultrasound systems; nuclear medicine imaging systems such as positron emission tomography (PET) systems, single photon emission computed tomography (SPECT) systems, cardiovascular imaging systems, and bone scanning systems.

Light imaging system 10 and the second imaging system 8 may produce spatial and/or functional information. Spatial information refers to information that contributes to a 2-D (pictorial) or 3-D geometric description of the object or its internal portions. A spatial representation provides a user with a 2-D or 3-D pictorial reference of the specimen. A 3-D geometric description typically comprises a reconstruction manufactured by processing data from multiple 2-D images. Functional information refers to information that contributes an item or activity of interest within the object. In one imaging embodiment, light imaging system 10 produces a 2-D or 3-D representation of a bioluminescent light source inside a mouse. The bioluminescent source may correspond to a wide variety of physiological issues being tracked or tested within the mouse, such as progress tracking of a particular cancer within a mouse. Some imaging applications include analysis of one or more representations of light emissions from internal portions of a specimen superimposed on a spatial representation of the specimen. The luminescence representation indicates portions of a specimen where an activity of interest may be taking place. Some imaging systems 8 or 10 produce both spatial and functional information. Light imaging system 10 for example is well-suited to generate both structural and functional information. Nuclear medicine uses radioactive substances to image a body and treat disease, and may provide information useful to both the physiology (functioning) and anatomy (spatial) of the object in establishing diagnosis and treatment.

At least one processor 2 is in logical communication with the light imaging system 10, in logical communication with the second imaging system 8, and in logical communication with the object handling system 6. Communication includes sending data to each system 6, 8 and 10 for purposes such as control of system components, position and motion control, regulation of image capture, etc. Communication also includes receiving data from system 6, 8 and 10 components for purposes such as image data acquisition, component control feedback, calibration, etc. Processor 2 cooperates with stored software and converts imaging sensor data provided by each of the imaging systems, such as camera output from light imaging system 10, into a form useful to a system user.

Processor 2 may combine data produced by light imaging system 10 and the second imaging system 8. One application of instructions implemented by processor 2 reconstructs a bioluminescent or fluorescent light source inside a living animal subject using one or more images of surface light emissions. This provides functional information useful in oncology, infectious disease research, gene expression research, and toxicology, for example. Light imaging according to the present invention is suitable for use with objects having a complex surface, such as an animal subject (e.g. a mouse or rat). As the term is used herein, a complex surface is any surface that cannot be described solely using a single polygonal description. The light reconstruction techniques employed herein also place no restrictions on the source distribution, such as the number of light sources in the object or the sizes and shapes of the sources, and no restrictions on the geometry, size or shape of the surface. And as will be described below, processor 2 may also combine spatial data from system 8 with light imaging data from system 10.

2. Light Imaging System

Figure 2A:
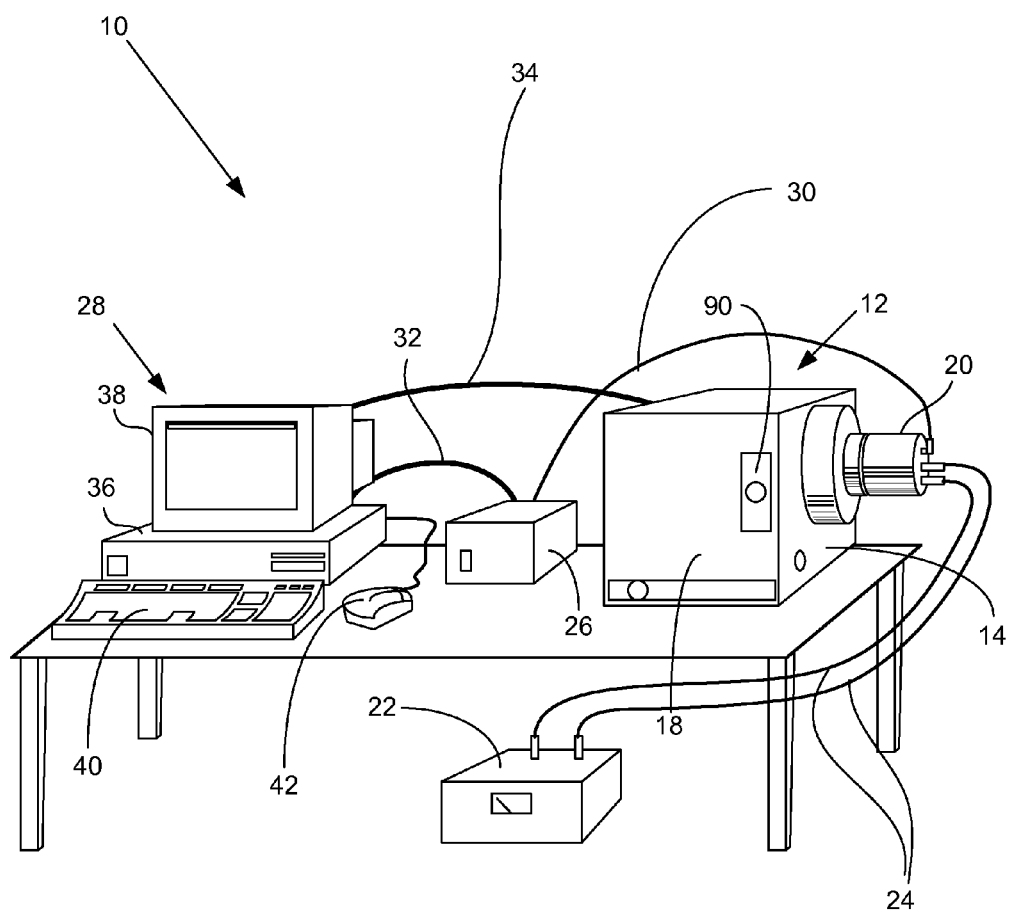
FIG. 2A is a perspective view of an imaging system adapted to produce a 2-D or 3-D representation of a light source located inside an object in accordance with one embodiment of the invention.

FIG. 2A illustrates an imaging system 10 adapted to produce a 2-D or 3-D representation of a light source located inside a sample in accordance with one embodiment of the present invention. Imaging system 10 may be used for a variety of imaging tasks including the capture of photographic, luminescent and structured light images. A computer 28 and its inclusive processor 2 working with imaging system 10 may perform processing and imaging tasks such as obtaining, analyzing and manipulating 2-D or 3-D light source representations.

Figure 2B:
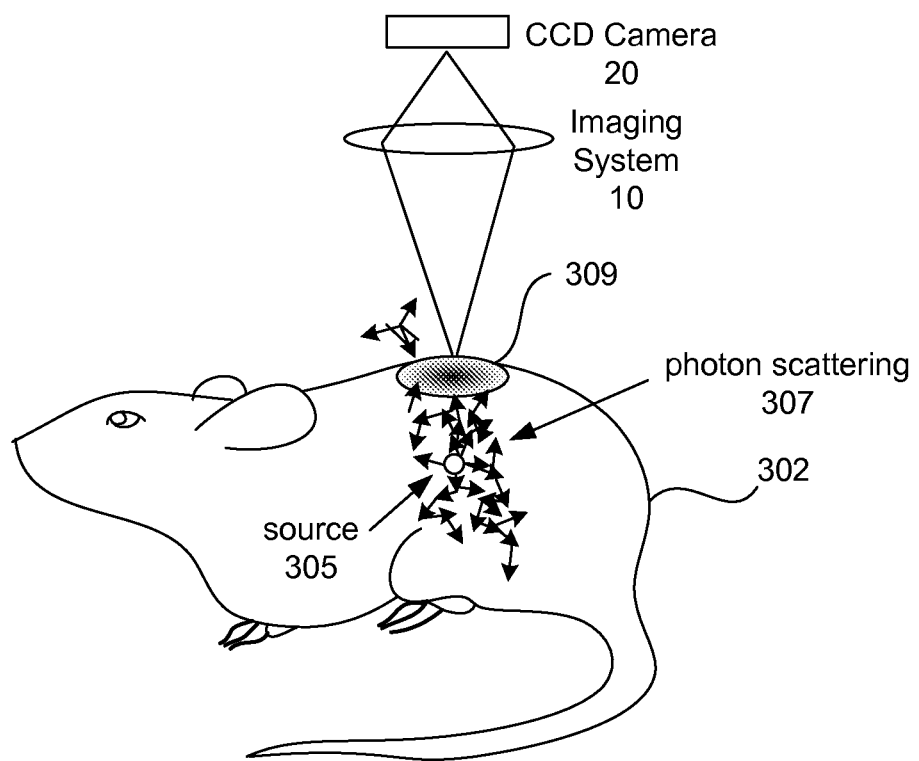
FIG. 2B shows a simplified illustration of light imaging in accordance with one embodiment of the present invention.

FIG. 2B illustrates a mammalian object 302 being imaged by camera 20 and light imaging system 10. The nature of mammalian tissue and many other turbid media causes photon scattering 307 for light traveling from a light source 305 within the object to the object surface 309, resulting in diffuse images on surface 309. Camera 20 captures a representation of light emitted from object 302 at surface 109. Using photon diffusion models and imaging data, a processor 2 in computer 28 operating on stored instructions may produce a 3-D representation for the location, size, and brightness of light source 305 from one or more surface 309 images.

Surface light emission data refers to information pertaining to light escaping an object interior. The light typically escapes from the object volume just below the surface. The light source may include luminescence from luciferase-expressing cells, fluorescence from fluorescing molecules, and the like. The object 302 generally refers to various mammalian subjects including mice and rats containing luciferase expressing cells or fluorescent reporters. In one application, sample 302 is a biological specimen containing light producing cells. The resulting luminescence image may therefore be captured without using any light sources other than the sample itself. Luminescence from sample 302 is recorded as a function of position to produce the luminescence image. One approach to generating such composite photographic/luminescence images is described in U.S. Pat. No. 5,650,135 issued to Contag et al. on Jul. 22, 1997. The entire disclosure of this patent is incorporated herein by reference for all purposes. Commonly owned U.S. Pat. No. 5,650,135 includes additional examples of analysis applications for a digital overlay image. The entire disclosure of this patent is incorporated herein by reference for all purposes.

Referring to FIG. 2A, system 10 images and processes low intensity light sources using a light sensitive camera 20. Light from the light source refers to photons and electromagnetic energy anywhere in the visible to near-infrared (NIR) part of the spectrum in the wavelength range of 400-950 nm It is understood that some intensities imaged and processed in system 10 are not readily detectable by human vision. For example, low intensity light emitted from a sample may have a surface radiance between about $10^3$ to about $10^{10}$ photons/second/centimeter squared/steradian. The lower end of this range is typically well below human detection levels.

In the illustrated embodiment, imaging system 10 includes an imaging chamber 12 adapted to receive a light-emitting sample in which low intensity light, e.g., luciferase-based luminescence, is to be detected. A high sensitivity camera 20, such as an intensified or a charge-coupled device (CCD) camera, couples with the imaging chamber 12. Camera 20 is capable of capturing luminescent, photographic (i.e., reflection based images) and structured light images of sample 302 within imaging chamber 12. A refrigeration device 22 cycles a cryogenic fluid to cool camera 20 via conduits 24.

An image processing unit 26 optionally interfaces between camera 20 and a computer 28 through cables 30 and 32, respectively. Computer 28, which may be of any suitable type, typically comprises a main unit 36 that contains hardware including a processor, memory components such as random-access memory (RAM) and read-only memory (ROM), and disk drive components (e.g., hard drive, CD, floppy drive, etc.). Computer 28 also includes a display 38 and input devices such as a keyboard 40 and mouse 42. Computer 28 is in communication with various components in the imaging chamber 12 via cable 34. In another embodiment, computer 28 is integrated with the imaging equipment in a single unit.

To provide control and communication for components in system 10, computer 28 is implemented with hardware and software for controlling and monitoring imaging components in system 10. Components controlled by the computer 28 may include camera 20, the motors responsible for camera 20 focus, the camera lens, f-stop, one or more motors coupled to a moveable stage (not shown) included in chamber 12, etc. Computer 28 also communicates with a display 38 for presenting imaging information to the user and also acts an interface to control the imaging system 10.

Computer 28 includes suitable processing hardware and software for image processing and data manipulation as described herein. For example, computer 28 may be configured with software to build a 3-D representation of a light source using light emission measurements from the surface of a sample. In addition, computer 28 may be configured to produce 3-D surface topography using 2-D structured light images taken from one or more positions of the stage in the interior cavity of chamber 12.

In one embodiment, 3-D light reconstruction techniques require bioluminescent surface radiance and surface topography measurements over the entire sample surface. In this case, imaging system 10 includes instructions and mechanisms for image capture of the object surface from multiple views and positions. Data from these multiple positions is then used to build a 3-D representation of the object. System 10 may image in 3-D according to the following scheme: 1) camera 20 remains fixed (when the various cables and supply lines for cooling the camera are too cumbersome to move during imaging); 2) the sample remains horizontal during imaging; 3) the imaging system obtains images of the objects from multiple views and positions; and 4) computer 28 builds a 3-D surface topography of the object using the multiple images according to reconstruction instructions stored in software.

Figure 2C:
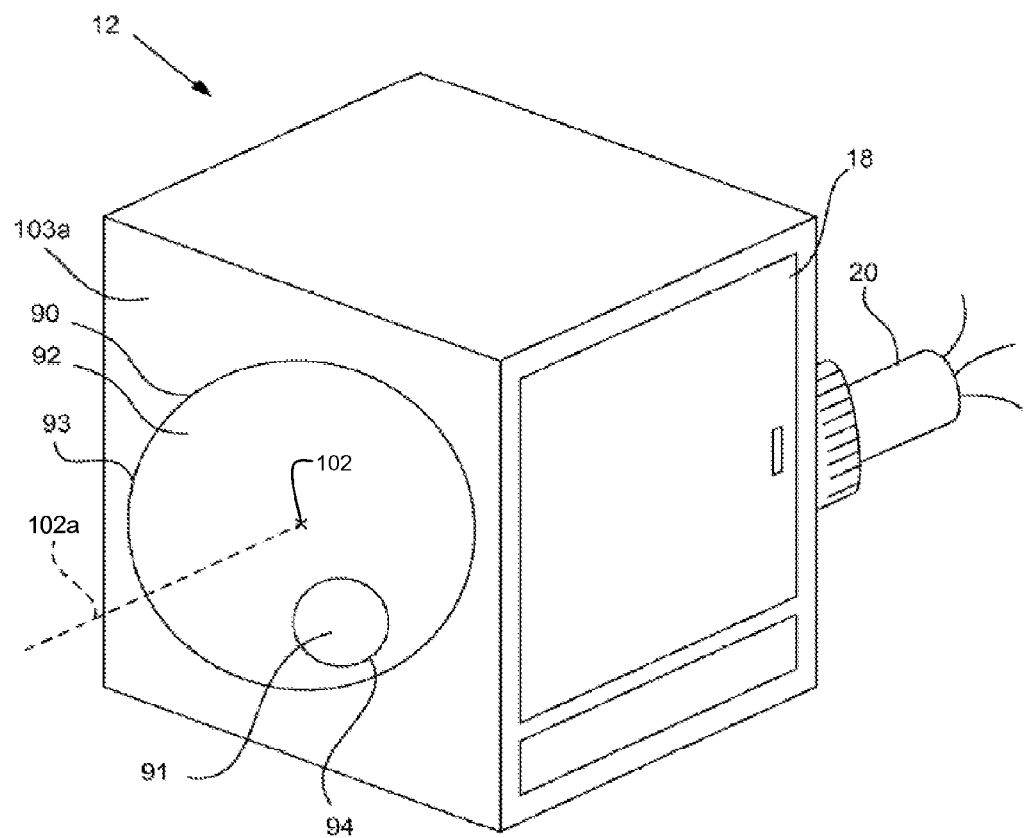
FIGS. 2C and 2D illustrate perspective and side views, respectively, of an exterior wall opposite a side mounted camera in accordance with one embodiment of the present invention.

The object or animal subject is typically loaded into imaging chamber 12 for image capture. Imaging chamber 12 provides multiple options to load an object into interior cavity 44. FIG. 2C illustrates a top perspective view of imaging chamber 12 in accordance with one embodiment of the present invention. Door 18 allows a user to manually open and close the door and place the object within interior cavity 44.

Figure 2D:
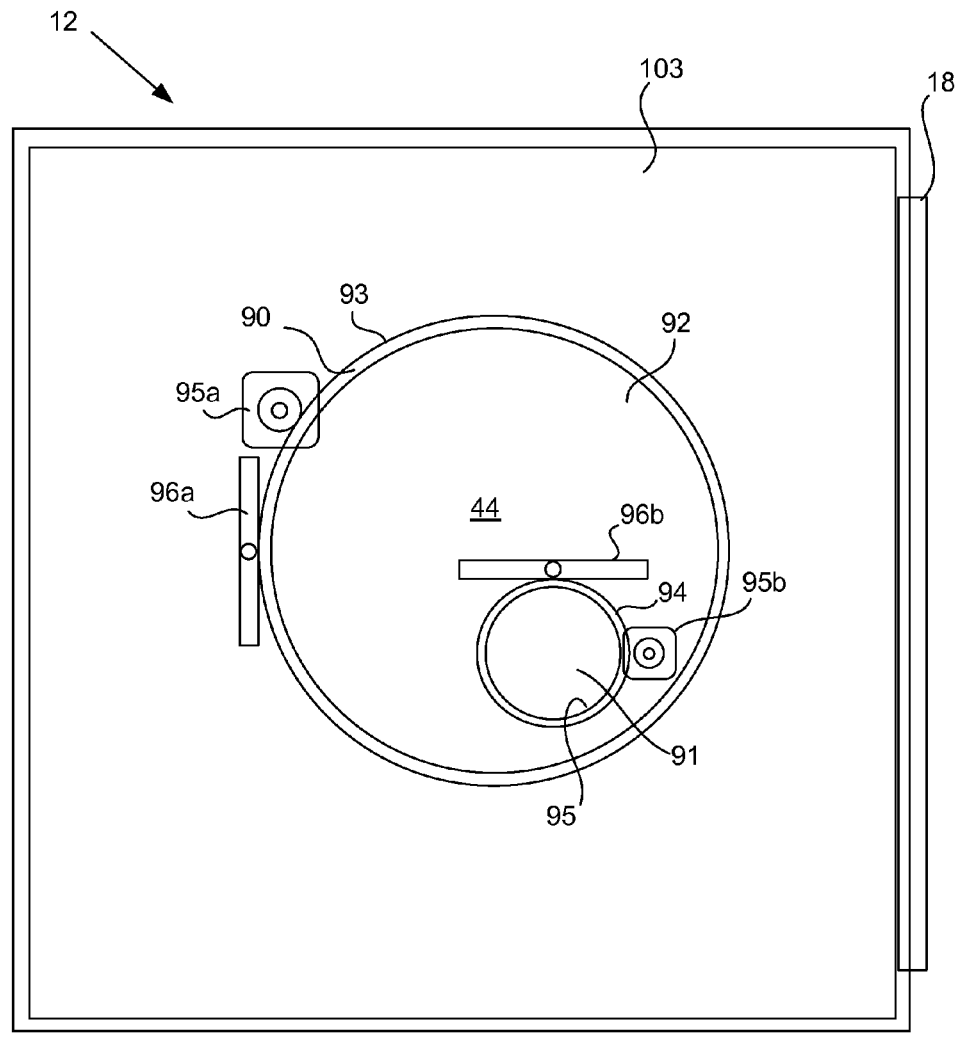

FIGS. 2C and 2D illustrate components that permit automated positioning of a stage 609 in an interior cavity 44 of chamber 12 in accordance with one embodiment of the present invention. Enclosure wall 103a lies opposite a sidewall that receives camera 20. A moveable interface 90 on wall 103a allows the automated object handling system 6 to insert a stage 609 into chamber 12 through a hole 91—and move the stage within chamber 12. Moveable interface 90 comprises wall 103a, wall 92, circular bearing 93, circular bearing 94, and an inner collar 95. Inner collar 95 defines the shape and size of hole 91 through which a portable stage 609 is received. When not in use, a cap (not shown) may cover hole 91 and seal any light from entering interior cavity 44. Circular bearing 93 is disposed between imaging chamber wall 103a and wall 92 and permits rotation between the exterior fixed wall 103 and moveable wall 92. Circular bearing 93 permits rotation between the wall 92 and inner collar 95. Cumulatively, bearings 93 and 94 allow hole 91 to trace a circular orbit about a center datum 102 and axis 102a extending through center datum 102. Datum 102 represents a fixed point relative to the motion of stage 609 and a common point for imaging the sample. Bearings 93 and 94 also allow inner collar 95 and stage 609 to maintain a constant angle relative to exterior wall 103 while it orbits datum 102. In one embodiment, stage 609 remains horizontal while orbiting datum 102. Bearings 93 and 94 also allow stage 609 to maintain a constant angle relative to the base of a robotic manipulator 502 interfacing with the inner collar 95.

Figure 1B:
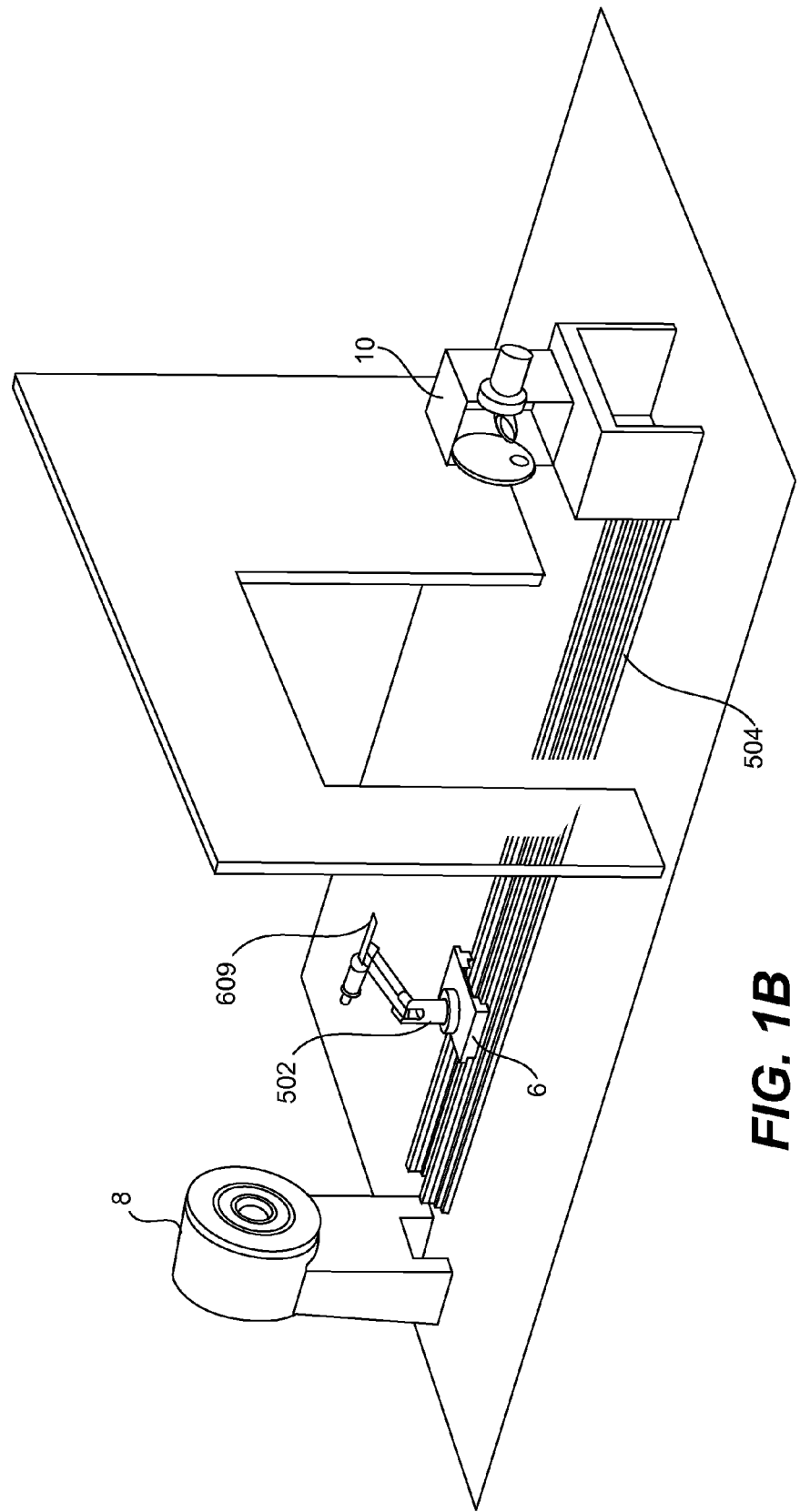
FIG. 1B illustrates a system for providing light and magnetic resonance imaging (MRI) imaging data in accordance with one embodiment of the present invention.

In one embodiment, object handling system 6 is configured to move a portable stage 609 within interior cavity 44. As shown in FIG. 1B, object handling system 6 comprises a track 504 and manipulator 502 for moving stage 609. Track 504 transports stage 609 to the vicinity of imaging system 10 and allows large movement for the object handling system 6 over large distances, such as between rooms. This finds use when imaging system 8 is an MRI system that prefers minimal ferrous metal nearby or in a room containing the MRI system. Manipulator 502 positions and aligns stage 609 in each system 8 and 10. Thus, manipulator 502 inserts stage 609 into hole 91 and also positions stage 609 relative to a tubular receiving area for the MRI imaging system 8. More specifically, manipulator 502 establishes the appropriate vertical and horizontal positioning between stage 609 and hole 91 and inserts stage 609 into chamber 12 via hole 91 for light imaging system 10.

Once inside chamber 12, the present invention contemplates multiple ways to position and move stage 609 within cavity 44. In one embodiment, bearings 93 and 94 are passive and the object handling system 6, e.g., via manipulator 502, moves stage 609 within interior cavity 44 relative to datum 102. In this case, a processor within computer 28 of FIG. 2B employs position control software to convert user input of a desired location for stage 609 to motor positions for motors included in manipulator 502. In another embodiment as illustrated in FIG. 2D, a motor 95a and sensor 96a are coupled to bearing 93 to control rotation of wall 92 relative to exterior wall 103, while a motor 95b and sensor 96b are coupled to bearing 94 to control rotation of inner collar 95 relative to wall 92. In this case, manipulator 502 remains passive while motors 95 control the orbital position of stage about fixed datum 102.

Moveable stage 609 allows a light image of the object, or portions thereof, to be captured by camera 20 from different views, angles, and positions within imaging chamber 12—without repositioning the posture of the object 302. Imaging a sample from multiple views provides additional information that helps build a 3-D internal light source representation. The additional information may be used to constrain 3-D reconstruction models stored in software on computer 28, thereby providing a more accurate 3-D representation of the object.

Figure 6A:
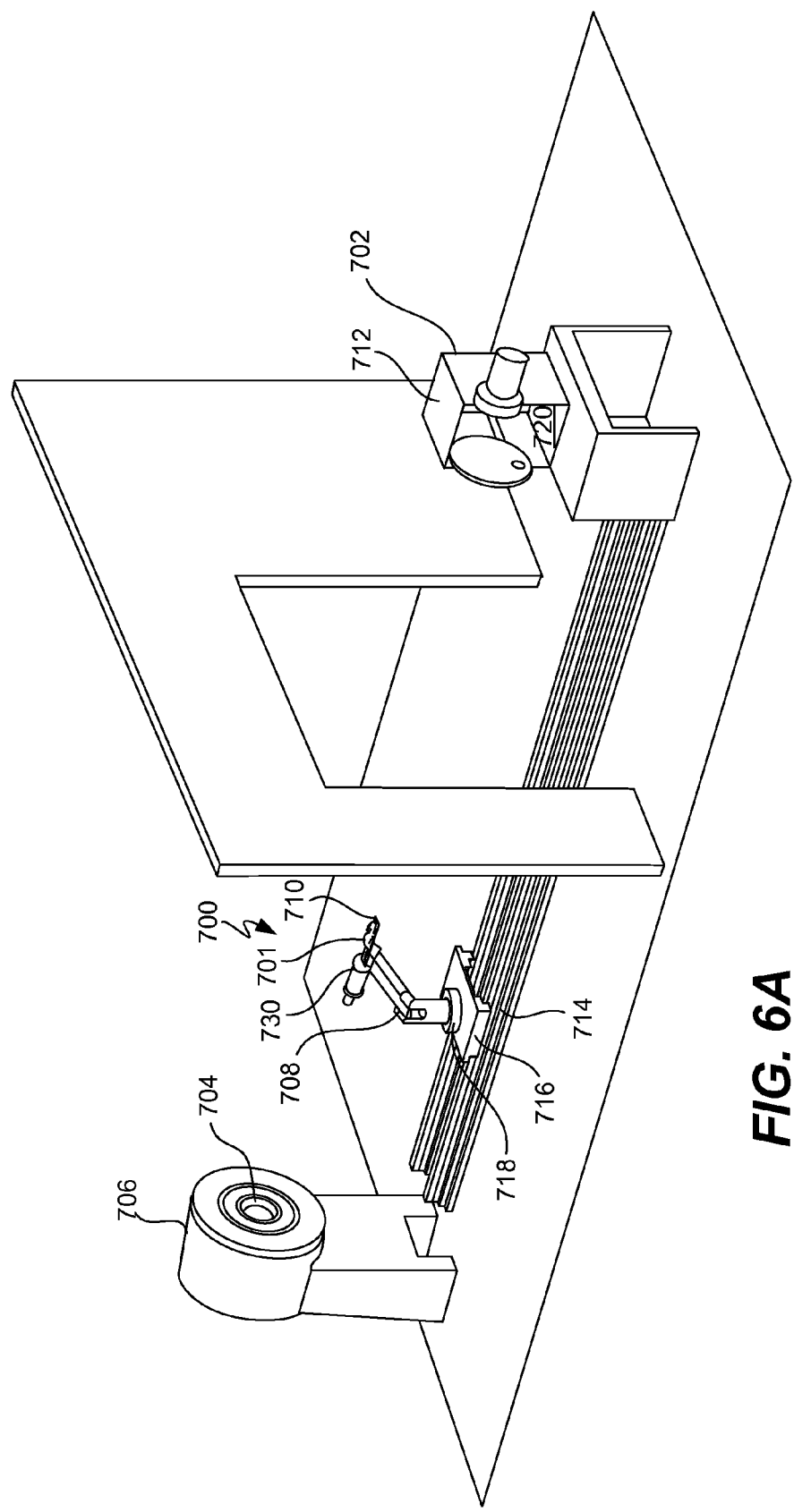
FIG. 6A illustrates an object handling system in accordance with one embodiment of the present invention.
Figure 6B:
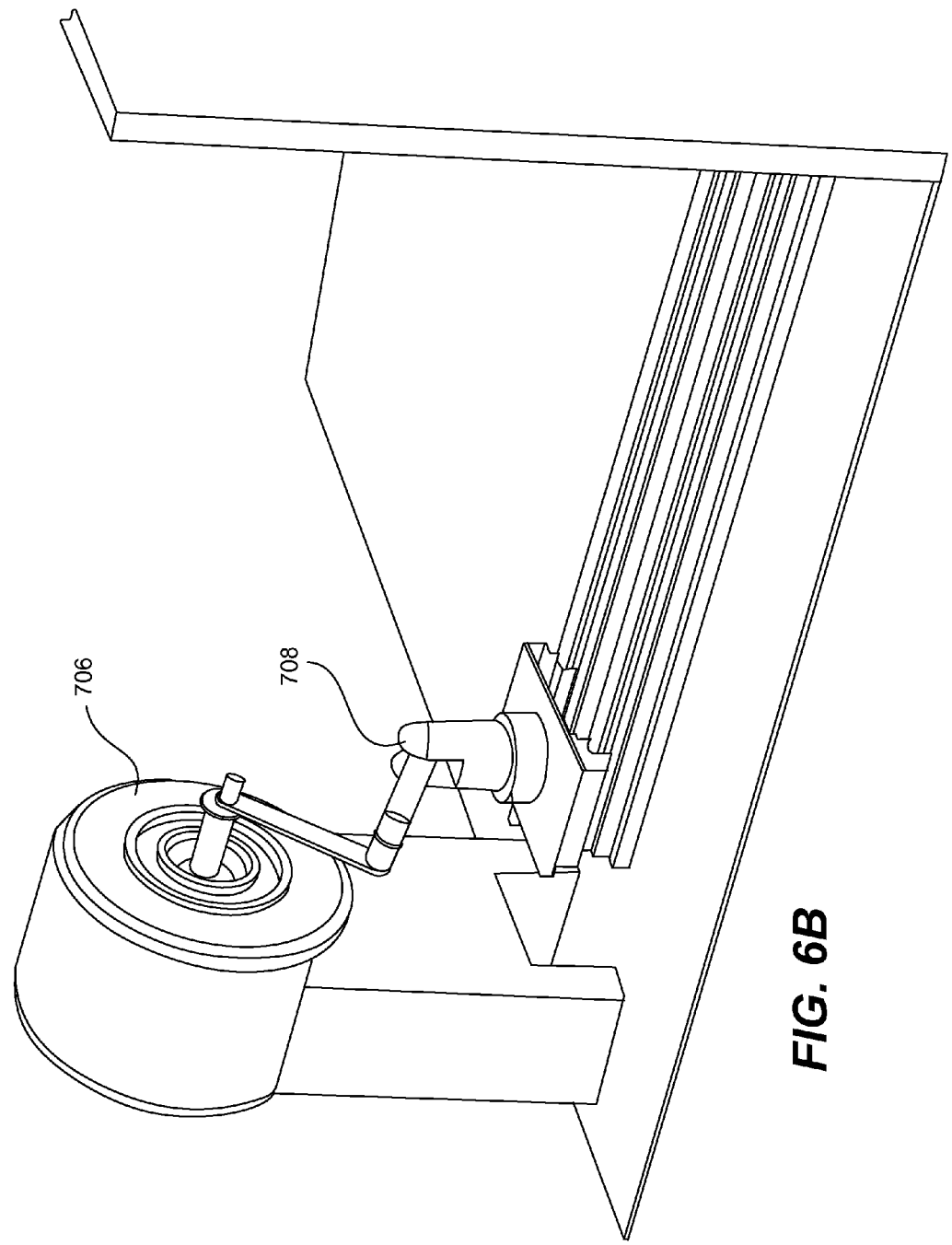
FIG. 6B illustrates the manipulator of FIG. 6A positioning a portable stage within an MRI receiving area in accordance with one embodiment of the present invention.
Figure 6C:
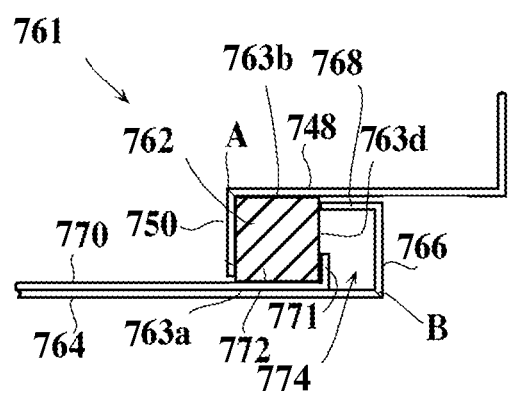
FIG. 6C shows a second wall around the perimeter of a hole, extending outwardly and generally perpendicular to wall in accordance with one embodiment of the present invention.

Manipulator 502 positions stage 609 in cavity 44. A variety of commercially available robotic manipulators 502 offer an end-effector positioning schemes suitable for positioning stage 609. One common scheme employs circular roll, pitch and yaw joints that allow upstream joints in the manipulator to achieve redundant positioning of stage 609. One or more upstream joints in manipulator 502 may be configured to move stage 609 in and out of chamber 12. A seal between chamber 12 and manipulator 502 effectively seals light from the exterior room from entering into chamber 12 when stage 609 is within chamber 12 (FIG. 6C).

Manipulator 502 may alternatively comprise linear actuators oriented substantially perpendicular to one another and attached to an upstream arm 506 of manipulator 502. Each linear actuator linearly positions stage 609 in an orthogonal direction. For instance, a first linear actuator provides vertical positioning for stage 609 while a second linear actuator provides horizontal positioning for the stage. The first linear actuator 206 has a relatively stationary portion attached to an upstream arm or base in manipulator 502 and a portion capable of vertical linear translation. The second linear actuator 208 may have a relatively stationary portion attached to the first linear actuator and a portion capable of horizontal linear translation. A third linear actuator may also be used to translate stage 609 parallel to the ground and to move stage in and out of chamber 12 through hole 91. An example of one such linear actuator suitable for use in manipulator 502 is a LC-33 produced by Thomson Industries of Port Washington, N.Y.

System 1 includes closed loop position control for stage 609 within interior cavity 44. More specifically, a user, via computer 28, inputs one or more positions for stage 609 along a substantially circular path about fixed datum 102. Alternatively, the user may provide a viewing angle for stage 609 relative to a fixed datum 102. Software included in computer 28 then converts the viewing angle into control signals for moving stage 609 from its current position to the desired position. Motors included in each of the actuators for manipulator 502 receive the control signals provided by computer 28 and position stage 609 accordingly. Manipulator 502 and each joint in manipulator 502 may include a position sensor in logical communication with a processor computer 28 to facilitate position feedback and control of stage 609.

Light imaging systems 10 suitable for use with the present invention are available from Xenogen Corporation of Alameda, Calif. Several light imaging systems suitable for use with the present invention are described in commonly owned pending U.S. patent application Ser. No. 09/905,668 entitled "Multi-View Imaging Apparatus", listing D. Nilson et al. as inventors and filed on Jul. 13, 2001, which is incorporated herein by reference for all purposes. 3-D imaging systems suitable for use with the present invention are further described in commonly owned pending U.S. patent application Ser. No. 10/606,976 entitled "Method and Apparatus for 3-D Imaging of Internal Light Source", listing D. Stearns et al. and filed on Jun. 25, 2003, which is also incorporated herein by reference for all purposes.

3. Secondary Imaging Systems

Figure 3:
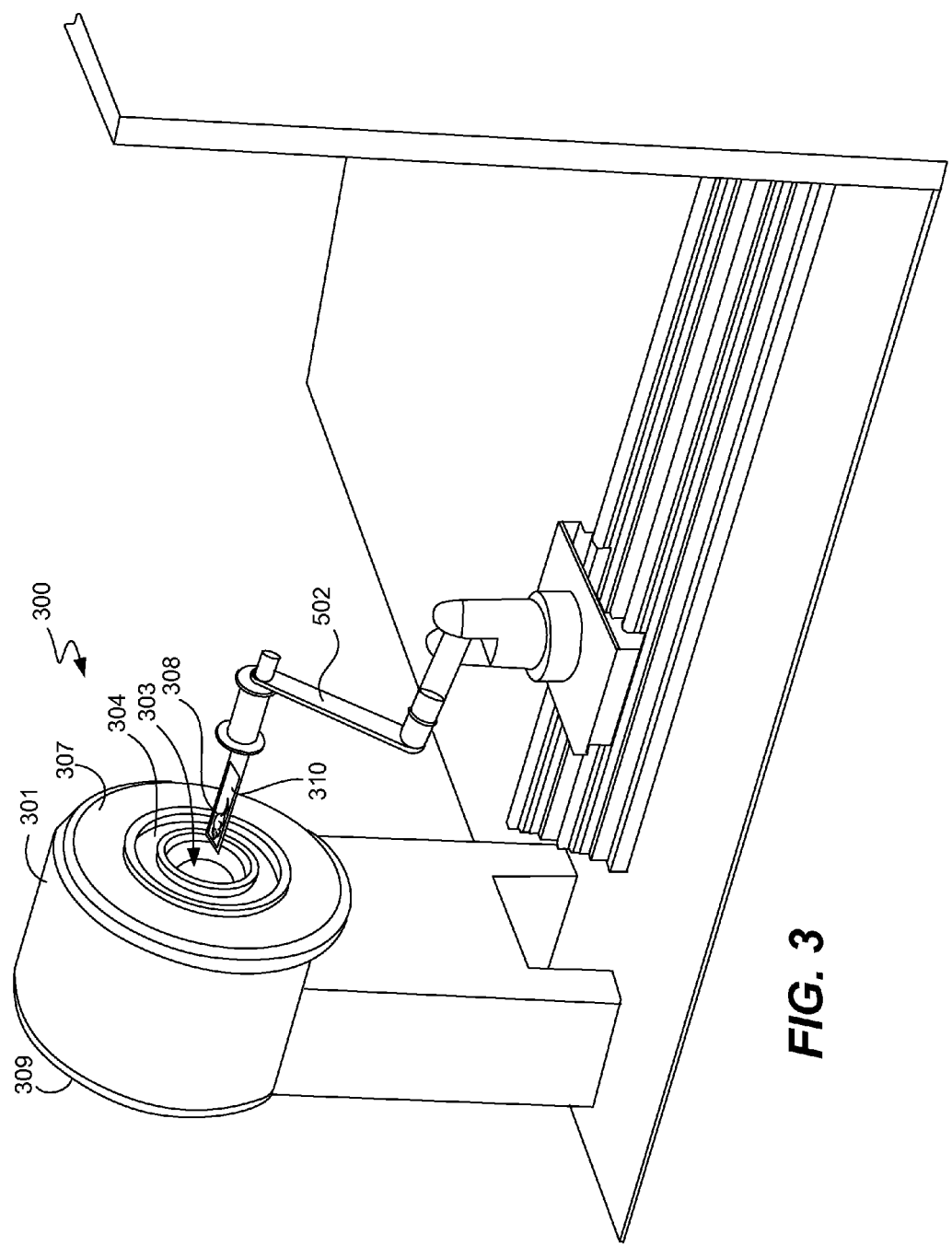
FIG. 3 illustrates a magnetic resonance imaging (MRI) system in accordance with one embodiment of the present invention.

In one embodiment, the second imaging system is a magnetic resonance imaging (MRI) system. FIG. 3 illustrates a magnetic resonance imaging (MRI) system 300 in accordance with one embodiment of the present invention. MRI system 300 typically comprises an MRI machine 301 and at least one processor (such as a processor included in computer 28 from FIG. 2A) in digital communication with the electronic components of MRI system 300. MRI machine 301 may vary in size, shape, and configuration, and some models include openness at the cylindrical sides. As shown, MRI machine 301 includes a horizontal tubular cavity 303 passing through a magnet 304. In this case, cavity 303 runs through magnet 304 from a front face 307 of MRI machine 301 to the back face 309. Tubular cavity 303 is also commonly referred to as the bore of magnet 304. An object 308 to be imaged rests on a stage 310 that is moved into tubular cavity 303. Object handling system 6 positions stage 310 and object 308 in tubular cavity 303. The type of exam being performed determines whether a mammalian sample 308 goes in head first or feet first, as well as how far into the magnet 304 they are positioned. Once the sample portion to be scanned is in the center or isocenter of the magnetic field for magnet 304, MRI scanning can begin.

MRI machine 301 may employ a magnet 304 from about 0.5-tesla to about 60.0-tesla, or about 5,000 to about 600,000 gauss. Using radio wave pulses of energy produced by magnet 304, MRI machine 301 scans the object and portions inside by proceeding through the sample's body point by point, building up a 2-D or 3-D map of tissue types currently being scanned. A processor 2 in electrical communication with machine 301 receives the magnetic output and operates on stored software instructions to integrate the scanned information and create 2-D images or 3-D models.

MRI system 300 provides a high level of spatial information relative to other imaging modalities. A 3-D model produced by MRI system 300 may be used to assist 3-D light reconstruction, e.g., to produce a surface representation useful for converting surface light emission data to light representations internal to object 308. A processor may also combine 2-D or 3-D spatial information provided by MRI system 300 with 3-D functional information provided by light imaging system 10. Coupled with the ability to track a biological entity of interest using the bioluminescence techniques described above, MRI system 300 and light imaging system 10 allow researchers to map progression of a biological entity through a particular internal portion of a sample 308 with previously unachievable fidelity and salience. In one application, spatial information from MRI system 300 is used to position 3-D light data relative to a specific anatomical structure of subject 308. For example, the physical size of a tumor within a mammalian sample 308 may be obtained from MRI system 300 and used to more accurately reconstruct 3-D light emission from the tumor provided by light imaging system 10.

Depending on the magnetic field strength used in MRI system 300, there may be ferrous metallic limitations associated with MRI system usage. In this case, stage 310 may be devoid of any ferrous metallic parts. In addition, magnet 304—such as a resistive based magnet that includes on/off control- may be shut off during sample transfer. One MRI system suitable for use with the present invention is the Bruker BioSpec available from Bruker BioSpin of Billerica, Mass.

In another embodiment, the second imaging system 8 is a computer tomography imaging (CT) system. Similar to MRI machine 300, a CT system offers a high level of spatial information, which may be combined with functional information collected by light imaging system 10.

Figure 4:
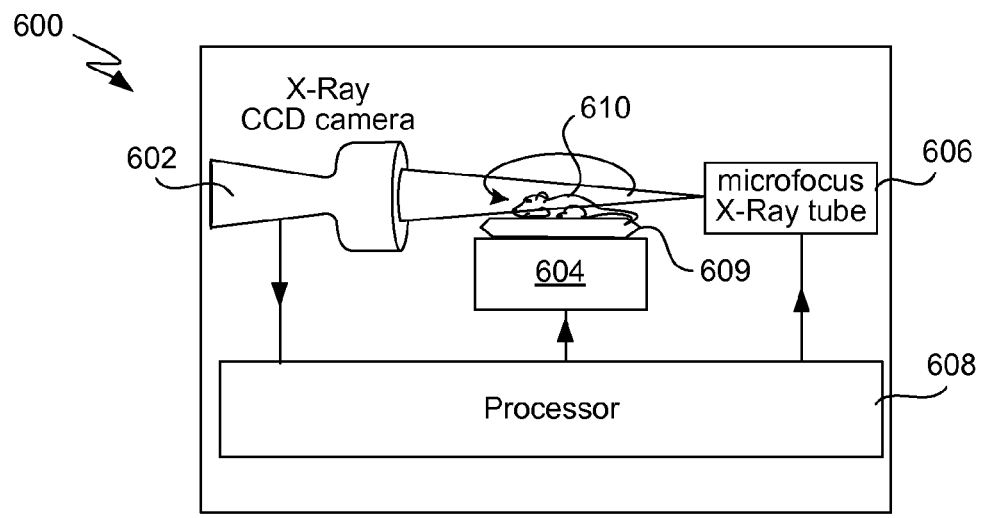
FIG. 4 illustrates a block representation of a computer topography (CT) system in accordance with one embodiment of the present invention.

FIG. 4 illustrates a block representation of a computer topography (CT) system 600 in accordance with one embodiment of the present invention. CT system 600 comprises an X-ray CCD camera 602, an object handling system 604, an array of microfocus X-ray tubes 606, and processor 608. Object handling system 604 positions an object 610 resting on a portable stage 609 in a receiving area such that X-rays emitted from CCD camera 602 pass through the object 610. The X-rays are then received by the microfocus X-ray tube array 606. Processor 608 digitally communicates with each of these devices and runs instructions from stored software to control X-ray emission from CCD camera 602, position sample 610, and to process data collected by the microfocus X-ray tube array 606.

CT system 600 yields a series of X-ray-based cross-sectional images of solid objects. X-ray intensity profile measurements are typically processed using reconstruction algorithms that produce an image representing a two-dimensional slice, or plane, through the material or portion scanned with X-rays. Each point of the slice corresponds to the material density. Processor 608 reconstructs a high-resolution image and details in the order of 1-10 μm can be detected with microfocus computer tomography and industrial microCT scanners, yielding volume element resolutions in the micrometer range. CT scanning is particularly useful to reveal internal anatomical features and portions of living and non-living samples.

CT system 600 also permits acquisition of 3-D volume and/or topology data. Consecutive cross-sectional images can be stacked to form a 3-D image of a portion of sample 610. Scanning the entire sample 610 permits a full volumetric image to be built. From the 3-D image data, instructions in software can be employed to find part boundaries and create computer models and representations of the entire sample 610 or particular portions of interest. One CT system suitable for use with the present invention is the MicroCAT as developed by researchers at Oak Ridge National Lab managed for the U.S. Department of Energy by UT-Battelle, LLC.

Similar to MRI system 300, CT system 600 provides a high resolution spatial information that compliments functional information produced by light imaging system 10. A 3-D model produced by CT system 600 may be used to assist 3-D light reconstruction, e.g., to produce surface or internal representations useful for converting surface light emission data to detailed light representations external or internal to the object. A processor may combine 2-D or 3-D spatial information provided by CT system 600 with 2-D or 3-D functional information provided by light imaging system 10. This ability for CT system 600 to produce high-resolution spatial information for an internal portion of sample 610 is useful to reconstruct high detail bioluminescent or fluorescent light sources, or a source distribution, inside a living animal subject. For example, three-dimensional light data internal to a mouse 610 may be matched with 3-D structural information generated by CT system 600 to produce a detailed picture of biological activity of an internal organ. This combination of spatial and functional information finds use in oncology, infectious disease research, gene expression research, and toxicology, for both snapshot imaging and progression tracking.

Nuclear medicine imaging systems 8 give researchers and imaging practitioners another imaging mode to look inside an object such as a mammalian body. Nuclear imaging systems employ radioactive substances that emit radioactive particles having known properties, and one or more sensors that detect the radioactive substances and their emissions. Conventional nuclear medicine imaging systems include: positron emission tomography (PET) systems, single photon emission computed tomography (SPECT) systems, cardiovascular imaging systems, and bone scanning systems. These systems use different properties of radioactive elements to create an image. Nuclear medicine imaging is useful for detecting tumors, aneurysms, irregular or inadequate blood flow to various tissues, blood cell disorders, and inadequate functioning of organs, such as thyroid and pulmonary function deficiencies. Any of these nuclear medicine imaging systems offer an alternative imaging system 8 that compliments the spatial and/or functional information produced by light imaging system 10. For example, both light imaging and nuclear medicine imaging may detect tumors in oncology applications.

Figure 5:
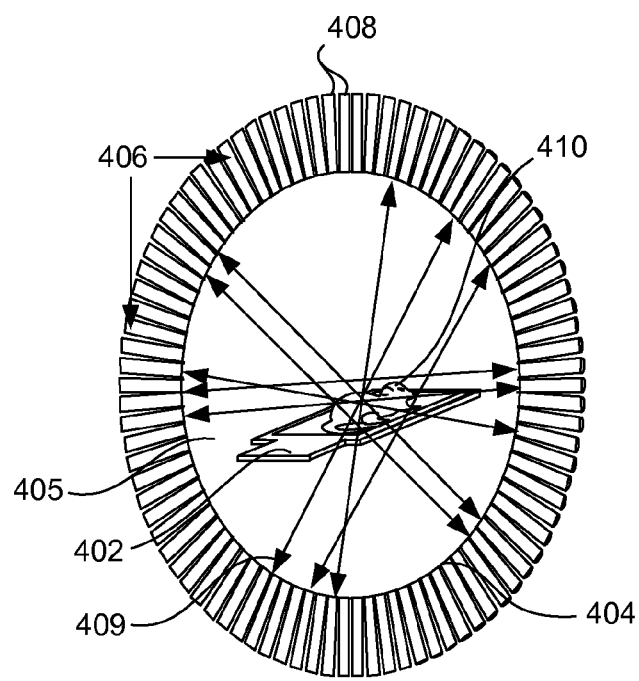
FIG. 5 illustrates imaging according to a positron emission tomography (PET) system in accordance with one embodiment of the present invention.

FIG. 5 illustrates imaging according to a PET system in accordance with one embodiment of the present invention. A PET system produces images of an object, or a portion thereof, by detecting radiation emitted from radioactive substances within the object. These substances are injected into the object, and are usually tagged with a radioactive atom, such as Carbon-11, Fluorine-18, Oxygen-15, or Nitrogen-13, that has a short decay time. In a PET scan, the object is injected with a radioactive substance and placed on a flat stage 402 that moves in increments through a tubular receiving area 405 of a "donut" shaped housing 404. Housing 404 contains a circular gamma ray detector array 406 that includes a set of scintillation crystals, each associated with a photomultiplier tube 408. The crystals convert gamma rays 409, emitted from inside the object 410, to photons of light. Photomultiplier tubes 408 convert and amplify the photons to electrical signals. These electrical signals are then processed by a processor in digital communication with the photomultiplier tubes that is configured to generate images based on the electrical signals from photomultiplier tubes 408. Stage 402 is then moved through the tubular receiving area 405 and the process is repeated, resulting in a series of thin slice images of object 410 over an internal portion of interest (e.g. a brain, chest, liver). The processor assembles these thin slice images into a three-dimensional representation of the internal portion. PET is particularly useful for providing images of blood flow and other biochemical functions, depending upon the type of molecule that is radioactively tagged. For example, PET images can show glucose metabolism or rapid changes in activity in various areas of a body.

Single Photon Emission Computed Tomography (SPECT) is a technique similar to PET, but the radioactive substances used in SPECT (Xenon-133, Technetium-99, Iodine-123) have longer decay times than those used in PET, and emit single instead of double gamma rays. A SPECT system is well suited to provide information about blood flow and the distribution of radioactive substances in the body. Its images have less sensitivity and are less detailed than PET images, but a SPECT system is less expensive than a PET system. Since light imaging system 10 is relatively inexpensive, a combined SPECT system 8 and light imaging system 10 offers a low cost multi-mode imaging alternative.

Figure 9:
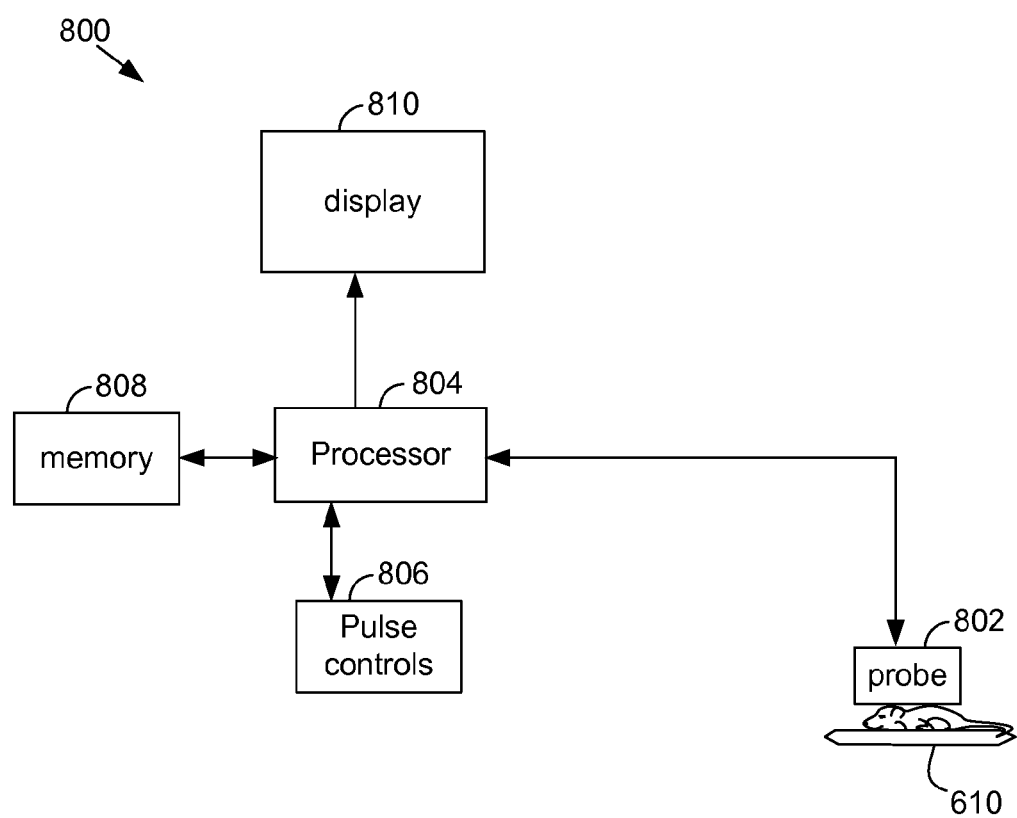
FIG. 9 illustrates an ultrasound imaging system in accordance with one embodiment of the present invention.

In another embodiment, the second imaging system 8 comprises an ultrasound imaging system. FIG. 9 illustrates an ultrasound imaging system 800 in accordance with one embodiment of the present invention. Ultrasound system 800 comprises a probe 802, processor 804, probe control 806, memory 808 and display 810.

Ultrasound system 800 transmits high-frequency (e.g., 1 to 5 megahertz) sound pulses in sample 610 using probe 802. Probe 802 generates sound waves that travel through sample 610 and hit a boundary between tissues (e.g. between fluid and soft tissue, soft tissue and bone). Some sound waves reflect back to probe 802, while others travel further until they reach another boundary and get reflected. Probe 802 detects the reflected waves and relays a corresponding signal to processor 804. The shape of probe 802 determines its field of view, while the frequency of emitted sound waves typically determine how deep the sound waves penetrate and the resolution of image data. In one embodiment, probe 802 generates and receives sound waves using piezoelectric effects. For example, probe 802 may contain one or more crystal elements, and in multiple-element probes, each crystal may include its own circuit. Multiple-element probes 802 allow an ultrasonic beam to be "steered" by changing the timing in which each element is pulsed. In addition to probes 802 that can be moved across the surface of sample 610, some probes 802 permit insertion through an opening of sample 610 (e.g., rectum, esophagus) to get closer to an organ being examined (e.g., prostate gland, stomach).

Processor 804 sends electrical currents to probe 802 that determine sound wave emissions, and receives electrical pulses from probe 802 that were created using the returning echoes. Processor 804 calculates the distance from probe 802 to the reflecting surface or boundaries (e.g., a tissue or organ) using the speed of sound in tissue (5,005 ft/s or 1,540 m/s) and the time of the each echo's return (usually on the order of millionths of a second). Processor 804 may then display the distances and intensities of echoes on display 810, forming a two dimensional image. Processor 804 may also be included in a computer system that contains electrical power supplies for probe 802, including any amplifiers and signal processing electronics. Processor 804 may also store the processed data and/or image in memory 808.

Probe controls 806 change the amplitude, frequency and duration of the sonic pulses emitted from transducer probe 802. Probe controls 806 also allow an operator to set and change the frequency and duration of ultrasound pulses, as well as a scan mode for system 800. Display 810 outputs an image from the ultrasound data provided by processor 804. Memory 808 may include a disk storage device (hard, floppy, CD) that stores the acquired images and instructions for system 800 data acquisition and 2-D or 3-D image reconstruction.

Ultrasound system 800 may produce 3-D spatial information. In this case, several 2-D images are acquired by moving probe 802 across a surface of sample 609 or rotating an inserted probe. The two-dimensional data is then combined by software stored in memory 808 to form a 3-D image. Some ultrasound imaging systems 800 offer 2-D or 3-D spatial image resolution of anatomical and physiological structures down to 30 microns. In addition, a user may view and analyze multiple arbitrary planes and perform volume measurements, such as determining a tumor volume. Ultrasound systems suitable for use with the present invention may include the Vevo 660 as provided by VisualSonics of Toronto, Canada. Ultrasound systems 800 are also relatively inexpensive; a combined ultrasound imaging system 800 and light imaging system 10 thus offers a low cost multi-mode imaging alternative.

4. Object Handling System

An object handling system moves the object to be imaged between the light imaging system 10 and second imaging system 8. FIG. 6A illustrates an object handling system 700 in accordance with one embodiment of the present invention. Object handling system 700 transfers an object 701 between an interior cavity 720 of light imaging system 702 and a receiving area 704 of a second imaging system 706.

Object handling system 700 comprises manipulator 708 and a portable stage 710 detachably coupled to manipulator 708. Manipulator 708 positions portable stage 710 near light imaging system 702 and the second imaging system 706, and may also provide precise positioning and orientation of portable stage 710 within the imaging or receiving areas of each system. As described above, each imaging system 8 comprises a receiving area that receives object 701, which may also correspond to or comprise the area in which the object is imaged, such as the tubular cavity 303 of an MRI machine. In this case, handling system 700 positions object 701 into the tubular cavity 303 and sets position of stage 710 and object 701 for MRI imaging. Manipulator 708 may include any number of arms and joints suitable for movement, positioning and orientation of portable stage 710 between or within the two imaging systems. For example, several commercial robotic manufacturers provide 5-and 6-degree of freedom manipulators suitable for payload weights ranging from about 1 kg to about 20 kg. One robotic manipulator suitable for use with object handling system 700 is the Denso Model VM available from Bruker BioSpin of Billerica, Mass.

When the second imaging system 706 is an MRI imaging system disposed in a second room for magnetic purposes, manipulator 708 may also include track 714 to allow for gross movement between rooms. An automated track interface 716 travels along track 714 and attaches to the bottom of base arm 718 of manipulator 708. Track interface 716: a) allows manipulator 708 to move large distances such as those used between rooms; and b) provides a stationary reference for the first rotary joint of base arm 718 (or any other first or base link in a robot). Computer control via one or more processors, such as those described above, may be used to move and position manipulator 708 and the automated track interface 716. Collectively, manipulator 708 and track 714 provide both large gross motion over a long distance and the ability to precisely position and orient portable stage 710.

Object handling system 700 may also be responsible for precise positioning of object 701 within the interior cavity of imaging chamber 712 or another imaging system. FIG. 6B illustrates the manipulator of FIG. 6A positioning the portable stage within an MRI receiving area in accordance with one embodiment of the present invention. In this case, manipulator 708 positions and orients portable stage 710 along a central axis of the cylindrical central cavity of MRI imaging system 706.

Portable stage 710, which is detachably coupled to the last arm or link of manipulator 708, supports object 701 during positioning by manipulator 708. Stage 710 refers generally to any flat surface or portable table suitable to support object 701. In one embodiment, the same stage 710 supports object 701 in each imaging system and during transfer between the imaging systems. Portable stage 710 may comprise a specialized robotic end effector designed for multiple imaging system usage. Object 701 rests on portable stage 710 and is positioned by object handling system 700—without substantially moving between imaging systems. Accordingly, object handling system 700 may insert and position stage 710 in interior cavity 720 of imaging chamber 712, remove stage 710 from the interior cavity 720, transfer stage 710 to receiving area 704 of second imaging chamber 706, and position stage 710 within receiving area 704—all without disturbing object 701. This is particularly advantageous for maintaining the positional accuracy provided by each imaging system or maintain an anesthesia state for a mammalian sample 701. A stage 710 comprising a substantially transparent mesh table or wire array (such as fishing line) supported by a non-metallic perimeter is suitable not to affect imaging in MRI system 300. In addition, the stage 710 or light imaging system 10.

To facilitate positional accuracy and object referencing between the two imaging systems, portable stage 710 comprises a light reference having a position detectable by the light imaging system 10 and a secondary reference having a position detectable by a second imaging system 8. Fixturing pegs and other fiducial tools are suitable to provide spatial referencing information. The pegs and tools may be marked with items that increase detectability for each imaging system. That is, the marks are configured to be optically detectable and distinguishable from the object 701 under test. Bull's eyes, crosses, bar-codes, known polygonal shapes, etc., having a known location on portable stage 710 are suitable as a positional reference for light imaging system 10. The secondary reference marking will depend on the type of second imaging system 8. Led markers may be suitable in conjunction with an x-ray system, for example. An MRI imaging system may reference a positioning peg having a hydrogen source or other distinct material of known density. In a specific embodiment, the reference position detectable by the light imaging system 10 and the reference position detectable by the second imaging system 8 includes the same position on stage 710.

Figure 6D:
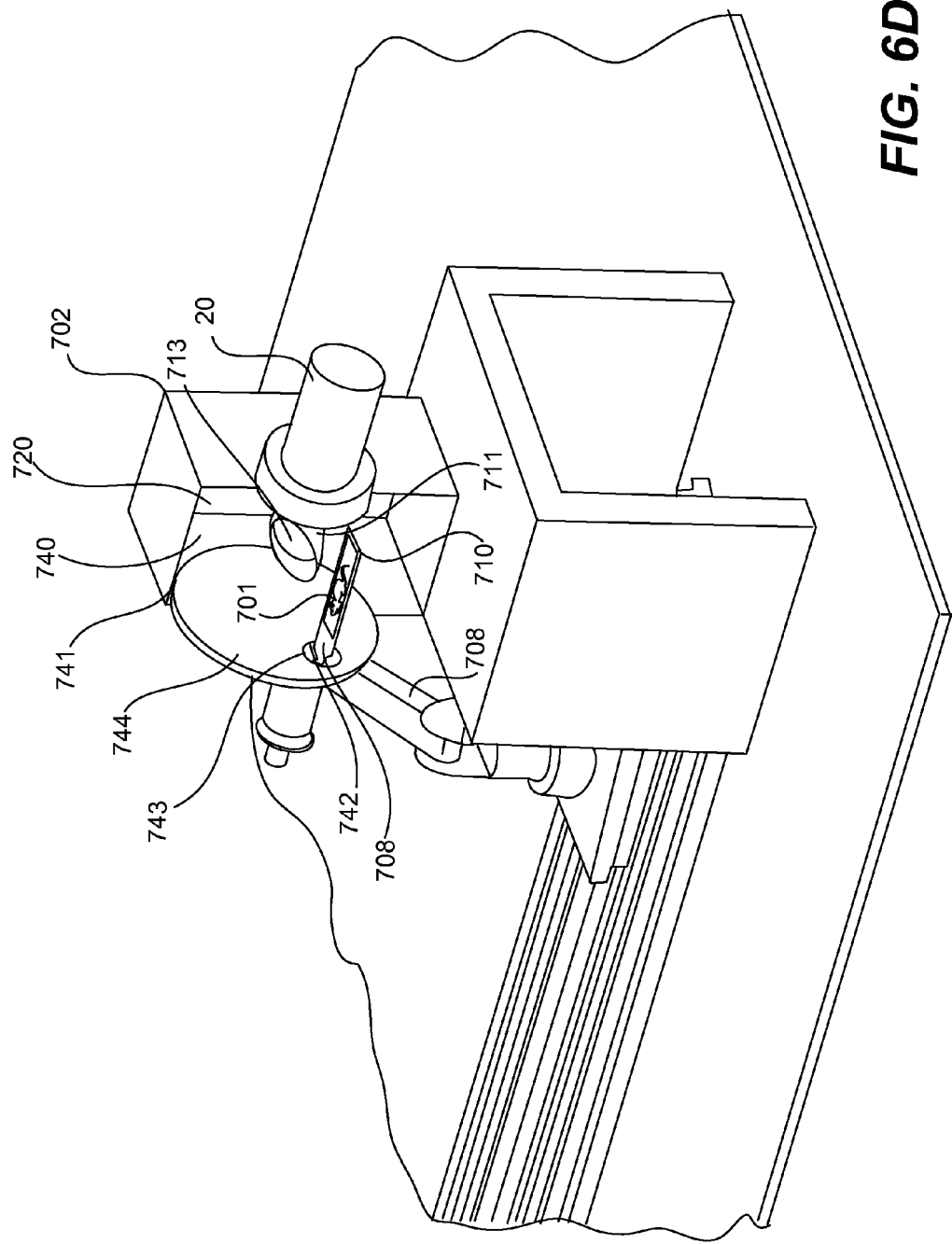
FIG. 6D illustrates the manipulator of FIG. 6A positioning a portable stage within an interior cavity of the light-imaging chamber of FIG. 6A in accordance with one embodiment of the present invention.

Object handling system 700 is also well suited to position object 701 in the interior cavity of the light imaging system 704. Referring to FIG. 6D, exterior wall 744 of chamber 712 includes a hole 742 that permits stage 710 access into interior chamber 720. A light imaging chamber 702 may be configured such that the interior cavity 720 is substantially light tight from the space outside imaging chamber 702. To accommodate the light tight requirements used in a light imaging system, the object handling system 700, light imaging chamber 702, or both, may include specialized adaptations such as light seals and other parts that maintain low light levels employed in imaging chamber 702. In one embodiment, the object handling system 700 and imaging chamber 702 comprise a complementary circular light seal configured to provide a substantially light tight barrier between interior cavity 720 of imaging chamber 712 and the space outside chamber 712 while portable stage 710 is within interior cavity 720. A plug may seal hole 742 when imaging system 10 is not in use. Without the plug, hole 742 enables manipulator 708 access to interior cavity 720.

FIG. 6C shows a light seal 761 established when manipulator 708 positions portable stage 710 within interior cavity 720 in accordance with one embodiment of the present invention. Wall 750 extends around the perimeter of hole 742, outward from and perpendicular to wall 744. Wall 750 includes a distal edge portion positioned substantially adjacent a rear wall 770 on manipulator 708 when manipulator 708 positions portable stage 710 within interior cavity 720.

Walls 748 and 750 of imaging chamber 712 cooperate with walls 764 and 766 on manipulator 708 to form a capture space 774, which extends perimetrically around the circular perimeter of hole 742. In this case, the capture space 774 has a rectangular cross-sectional area where a vertex A formed by box walls 748 and 750 opposes a vertex B formed by door walls 764 and 766. Walls 766, 764 and 770 on manipulator 708 cooperate with external surfaces on light imaging box walls 748 and 750 to define a capture space 772.

A compressible material 762 attaches to wall 764 of manipulator 708 within capture space 772. Compressible material 762 prevents light penetration by light from the ambient room into interior cavity 720. When manipulator 708 positions portable stage 710 within interior cavity 720, compression of material 762 creates a substantially "light-tight" seal. Compressible material 762 thus minimizes the amount of external light that enters cavity 720 when manipulator 708 positions portable stage 710 within interior cavity 720. In one embodiment, collar wall 770 is adapted to compress the compressible material 762 substantially along a first side 763a of compressible material 762 and wall 748 is adapted to compress compressible material 762 substantially along a side portion 763b when manipulator 708 positions portable stage 710 within interior cavity 720. Compressible material 762 comprises a non-transparent, preferably black, and resiliently deformable material.

Manipulator 708 comprises a front wall 764, a side wall 766 and a second wall segment 768. A collar rear wall 770 attaches to an inner surface of collar 764 included manipulator 708 to facilitate light sealing with the light imaging chamber. In a specific embodiment, manipulator 708 collar wall 770 has a wall section 771 that extends perimetrically around hole 742 when manipulator 708 positions portable stage 710 within interior cavity 720. In another embodiment, the wall section 771 extends toward the body front wall 748 at an orientation engaging a fourth side portion 763d of the compressible material 762 between a second side portion 763b thereof engaged by the body front wall 748 and a first side portion 763a of the compressible material 762 engaged by the manipulator 708 collar wall 770.

Figure 6E:
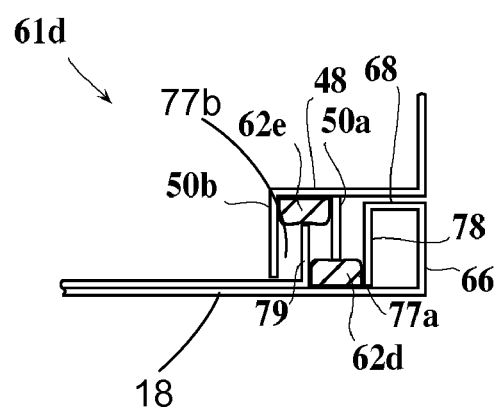
FIG. 6E illustrates a light-tight seal in accordance with another embodiment of the present invention.

FIG. 6E illustrates a light-tight seal 61d in accordance with another embodiment of the present invention. Light-tight seal 61d includes two compressible materials, 62d and 62e, retained inside two channels 77a and 77b, respectively. Channel walls 78 and 79, both of which extend from manipulator 708, form channel 77a Channel 77b is formed by generally parallel channel walls 50a and 50b, both of which extend from the front wall 48 of chamber 12 and substantially perimetrically around hole 91. In this case, channel wall 79 is received in channel 77b when manipulator 708 inserts stage 310 in cavity 44. Thus, channel wall 79 engages the second compressible material 62e such that light entering the second channel 77b from the exterior of the body 14 is intercepted by the second compressible material 62e.

The materials 62d and 62e fill only a portion of the channels 77a and 77b respectively. In one embodiment, materials 62d and 62e fill at most about ¾ of the channel 75 depth as measured from the walls 70 and 48 respectively. In another embodiment, materials 62d and 62e fill at most about ½ the channel depth. In a specific embodiment, materials 62d and 62e fill at most about ¼ the channel depth. Thus, the interengaged walls 50a and 50b and channel walls 78 and 79 substantial overlap, relative their respective depth, when manipulator 708 inserts stage 310 in cavity 44. Any light attempting to penetrate the light barrier requires at least six right angle turns (including four through the compressible materials 62d and 62e) before it can enter the interior cavity 44 from the ambient room.

Light-tight seal 61d further includes manipulator side wall 66 extending outwardly from the manipulator 708 toward the front wall 48 when manipulator 708 inserts stage 310 in cavity 44. In this case, manipulator side wall 66 is positioned perimetrically outside and generally parallel to the channel walls 78 and 79 and the interengaging front wall 50. Manipulator 708 further includes a second wall segment 68 extending from side wall 66, and oriented substantially adjacent to the front wall 48 when manipulator 708 inserts stage 310 in cavity 44. As shown, the second wall segment 68 extends in the inward direction toward interengaging front wall 50 and the channel walls 78 and 79.

FIG. 6D illustrates manipulator 708 positioning portable stage 710 within interior cavity 720 of light imaging chamber 712. In this case, manipulator 708 moves portable stage 710, and object 701 resting thereon, in two dimensions within the interior cavity of the light imaging chamber 712. More specifically, manipulator 708 moves portable stage 710 in a circular orbit about a camera or common viewing datum in chamber 712. As the object may be variably and multiply located within chamber 712, a light transport device 711 transmits light emitted or reflected from the object to a common datum associated with a side mounted camera 20. In one embodiment, the light transport device 711 comprises a mirror 713 that rotates with stage 710 about the common datum and so as to always face object 701 and reflect light from the object on stage 710, along the common datum, and into fixed camera 20. This allows a light image of the object, or portions thereof, to be captured by a camera from different views, angles, and positions within imaging chamber 12 without repositioning the posture of the object 701 on stage 710 or moving camera 20.

To facilitate such movement, an exterior wall 740 of imaging chamber 710 comprises a) a moveable interface having a hole 742 that receives portable stage 710 therethrough, b) a first circular bearing 741 disposed between exterior wall 740 and a wall 742 of the moveable interface; and c) a second circular bearing 743 that permits rotation between wall 742 and the object handling system 708. Together, circular bearings 741 and 743 permit opposing free rotation—which eliminates any relative rotation between stage 710 and chamber 712—and permits stage 710 to remain horizontal while moving in an orbital path.

Portable stage 710 allows imaging to be conducted in multiple imaging systems 8 and 10 without disturbing the object 701. For an animal 701, turning or flipping the animal over to view a ventral side results in a significant shift in the animal's internal organ position, which could affect observation. Imaging in each of the systems 8 and 10 and transfer between the systems may require significant time. Obtaining a luminescence representation may also involve image capture over an extended period, such as several minutes. To prevent movement of a living specimen during imaging, object handling system 700 may comprise an anesthesia delivery system that delivers anesthesia gas to outlets in proximity to one or more living specimens. The anesthesia delivery system is also useful for anesthetizing living specimens during transfer between imaging systems. An exemplary anesthesia delivery system and gas delivery system suitable for use with the present invention are described in commonly owned co-pending U.S. Pat. No. 10/081,040, entitled "Multiple Output Anesthesia System" by Richard George Dalgetty et al. filed on Feb. 20, 2002, which is incorporated herein by reference for all purposes.

Figure 7:
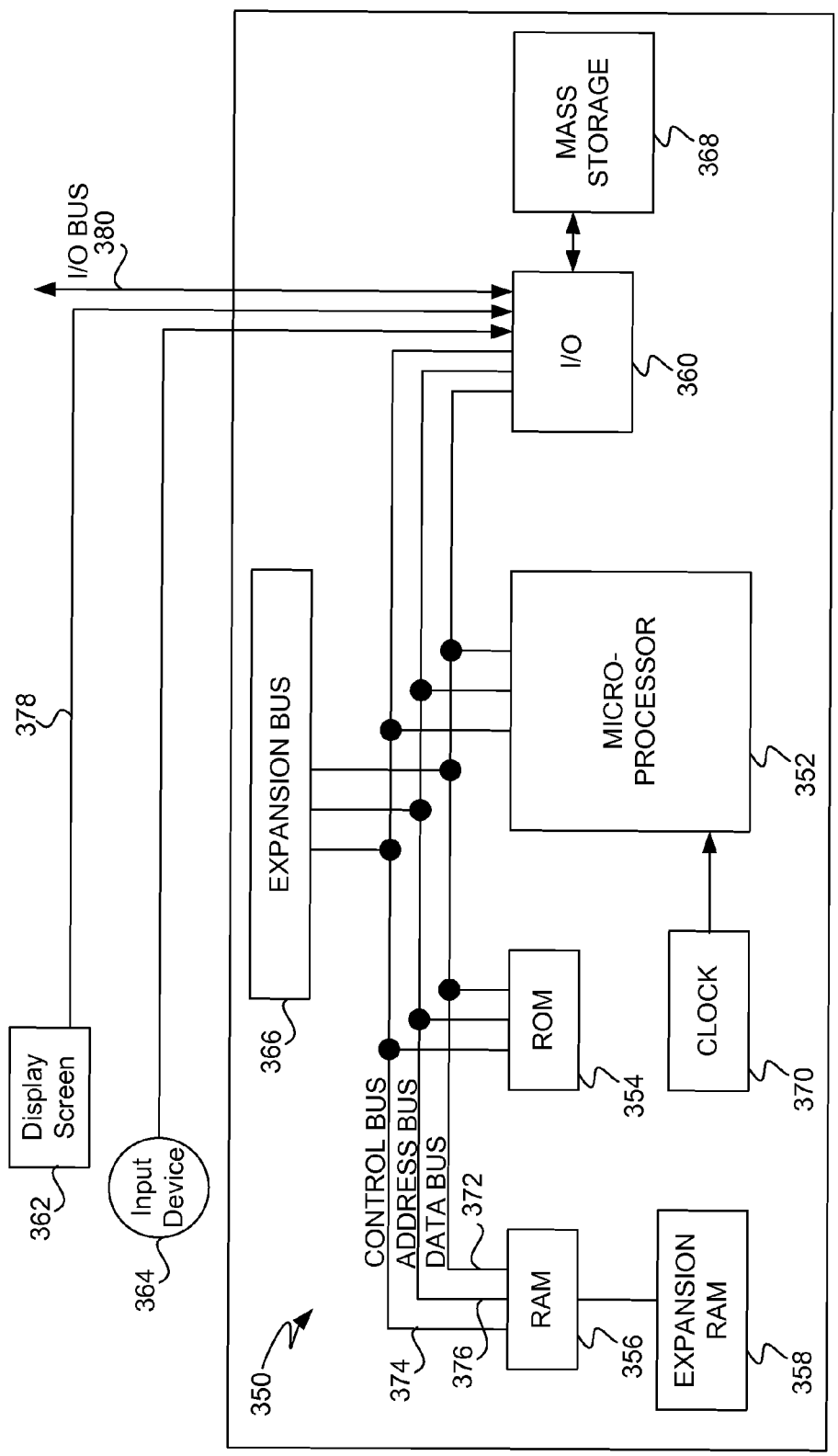
FIG. 7 illustrates an exemplary computer system in accordance with one embodiment of the present invention.

Imaging techniques described herein are implemented in conjunction with a suitable processor or computer-based apparatus. Referring to FIG. 7, an exemplary computer system 350 includes a central processing unit (CPU) 352, read only memory (ROM) 354, random access memory (RAM) 356, expansion RAM 358, input/output (I/O) circuitry 360, display assembly 362, input device 364, and expansion bus 366. Computer system 350 may also optionally include a mass storage unit 368 such as a disk drive unit or nonvolatile memory such as flash memory and a real-time clock 370. Mass storage unit 368 may include units which utilize removable computer readable media, such as floppy disks, optomagnetic media, optical media, and the like for the storage of programs and data.

CPU 352 is preferably a commercially available microprocessor such as one of the Intel (including Pentium™) or Motorola family of chips, a reduced instruction set computer (RISC) chip such as the PowerPC™ microprocessor available from Motorola, Inc, or any other suitable processor. CPU 352 is coupled to ROM 354 by a data bus 372, control bus 374, and address bus 376. ROM 354 may partially contain the basic operating system for the computer system 350. CPU 352 is also connected to RAM 356 by busses 372, 374, and 376 to permit the use of RAM 356 as scratch pad memory. Expansion RAM 358 is optionally coupled to RAM 356 for use by CPU 352. CPU 352 is also coupled to the I/O circuitry 360 by data bus 372, control bus 374, and address bus 376 to permit data transfers with peripheral devices.

Via suitable I/O inputs, CPU 352 is in logical communication with light imaging system 10, in logical communication with the second imaging system 8, and in logical communication with the object handling system 6. CPU 352 operates on stored instructions to combine spatial information provided by the second imaging system 8 with information provided by the light imaging system 10. ROM 354 may store the image processing instructions. ROM 354 may also store protocol for controlling the object handling system 6 according to positioning needs of the multi-modal imaging system, e.g., store proprietary robotic control commands that dictate robot movement according to positioning instructions for the imaging.

I/O circuitry 360 typically includes a number of latches, registers and direct memory access (DMA) controllers. The purpose of I/O circuitry 360 is to provide an interface between CPU 352 and such peripheral devices as display assembly 362, input device 364, mass storage 368, and/or any other I/O devices in imaging systems 8 and 10. I/O circuitry 360 may also include analog-to-digital (A/D) converters, digital-to-analog (D/A) converters, as well as other control circuits for controlling and receiving feedback data from the I/O devices. Display assembly 362 of computer system 350 is an output device for displaying objects and other visual representations of data.

The screen for display assembly 362 can be a device that uses a cathode-ray tube (CRT), liquid crystal display (LCD), or the like, of the types commercially available from a variety of manufacturers. Input device 364 can be a keyboard, a mouse, a stylus working in cooperation with a position-sensing display, or the like. Alternatively, input device 364 can be an embedded RF digitizer activated by an "active" RF stylus. As a further alternative, input device 364 may be any type of switch capable of communicating a test subject's response to computer system 350. Therefore, as used herein, the term input device will refer to any mechanism or device for entering data and/or pointing to a particular location on a screen of a computer display. One or more input devices may be provided to control computer 350 and/or to receive responses from the test subject. The aforementioned input devices are available from a variety of vendors and are well known in the art.

Some type of mass storage 368 is generally considered desirable. However, mass storage 368 can be eliminated by providing a sufficient amount of RAM 356 and expansion RAM 358 to store user application programs and data. In that case, RAMs 356 and 358 can optionally be provided with a backup battery to prevent the loss of data even when computer system 350 is turned off. However, it is generally desirable to have some type of long term mass storage 368 such as a commercially available hard disk drive, nonvolatile memory such as flash memory, battery backed RAM, PC-data cards, or the like.

Regardless of computer system 350 configuration, it may employ one or more memories or memory modules configured to store program instructions for robotic control, obtaining a three-dimensional representation of a light source, and other imaging functions of the present invention described herein. Such memory or memories may also be configured to store data structures, imaging data, or other specific non-program information described herein. It should be borne in mind that although computer system 350 is discussed in some detail herein to facilitate discussion, the invention may be practiced using a variety of suitable computer-implemented techniques. In general, any suitable computer system may be employed for obtaining a three-dimensional representation of a light source located inside a sample.

Because information and program instructions may be employed to implement the systems/methods described herein, the present invention relates to machine-readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 8:
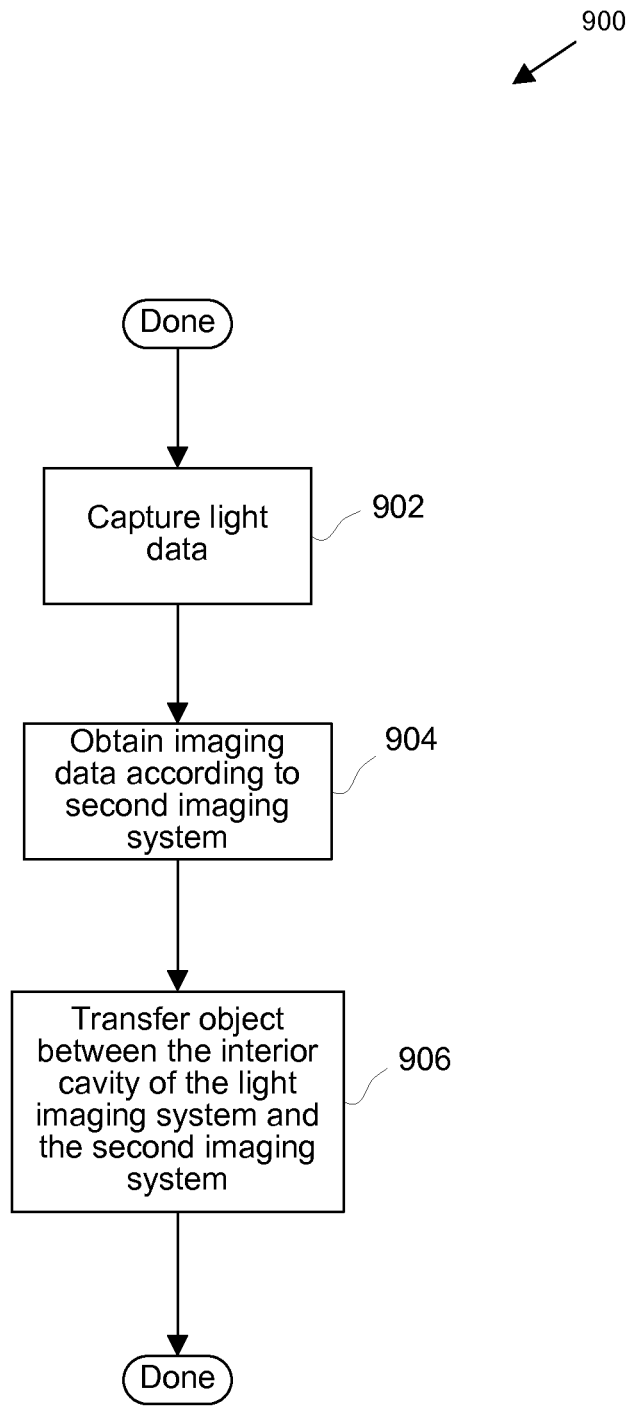
FIG. 8 illustrates a process flow for obtaining multiple mode representations of an object in accordance with one embodiment of the present invention.

FIG. 8 illustrates a process flow 900 for obtaining multiple types of imaging data for an object in accordance with one embodiment of the present invention. Processes in accordance with the present invention may include up to several additional steps not described or illustrated herein in order not to obscure the present invention.

Process flow 900 begins by capturing light data emitted from a light source located inside the object while the object is in the interior cavity of a light imaging system (902). For imaging system 10, the surface light emission data is contained in images captured by camera 20. The images include a set of measurements of the light emission over one or more portions of the surface. In one embodiment, multiple images of the sample are obtained from multiple views of the sample relative to a camera. In this case, each image provides a different two-dimensional view of the surface light emission from the sample. Multiple images may be taken to provide additional data from multiple angles.

Process flow 900 then continues by obtaining imaging data of an internal portion of the object while the object is in a receiving area of a second imaging system (904). When the second imaging system is a magnetic resonance imaging system, obtaining imaging data comprises receiving the imaging data using a magnetic resonance imaging magnet. For a computer tomography imaging system, obtaining imaging data generally comprises receiving the imaging data using an array of X-ray sensors that detect X-rays emitted from the object.

It is understood that light imaging or the imaging in the second imaging system occurs in no set order. Regardless of which imaging system is used first, the object is transferred between the interior cavity of the light imaging system and the receiving area of the second imaging system (906). In one embodiment, the transfer occurs without substantially moving the object on the portable stage that the object rests upon. Transfer may also comprise sealing the light imaging chamber, while the portable stage is within the interior cavity of the light imaging chamber, using a light seal included in the object handling system.

Process flow 900 may also combine the output of each imaging system. For example, software and user input may be used to combine spatial data provided by the magnetic resonance imaging system with functional data provided by the light imaging system. In some cases, software may combine three-dimensional spatial information provided by an MRI or computer tomography system with three-dimensional functional information provided by the light imaging system.

3-D light reconstruction techniques may be employed to reconstruct light data emitted from a sample surface. The reconstruction techniques use data that provides information about the geometry of the sample and the spatial distribution of the light emission from the sample surface. This may include data that comprises a) a surface representation of the sample (e.g., from the second system 8), and b) a set of measurements (e.g. images) of the light emission over at least a portion of the surface. One format for this data comprises (1) a surface representation defining the surface of the sample, (2) a set of light emission images from the sample surface, and (3) a set of parameters that define the spatial relationship between the sample and each image. 3-D light reconstruction then comprises converting surface light image data into light data internal to the object surface to obtain a three-dimensional representation of the internal light source. This may include creating a set of volume elements within the object.

A surface representation may also be obtained via the secondary imaging system or structured light techniques. For example, three-dimensional spatial information provided by a computer tomography imaging system 8 may be used to build a surface representation. To facilitate light 3-D light reconstruction, the surface representation is divided into surface elements or a suitable surface mesh approximating the actual surface of the sample. For example, the surface mesh may be defined by a set of connected polygons, where each polygon is a surface element. The number of surface elements varies according to the object size and a desired solution accuracy. Accuracy of a surface representation generally improves by increasing the number of surface elements.

While this invention has been described in terms of several preferred embodiments, there are alterations, permutations, and equivalents which fall within the scope of this invention which have bepen omitted for brevity's sake. For example, although imaging chamber 12 is described with multiple options for object access into interior cavity 44, it is understood that the present invention may include only one form of access (e.g., manual access or automated access, not both). It is therefore intended that the scope of the invention should be determined with reference to the appended claims.

What is claimed is:

1. A multi-modal imaging system configured to provide multiple types of imaging data for an internal portion of an object being imaged, the multi-modal imaging system comprising:

a light imaging system configured to provide three-dimensional functional information related to light emitted from a light source located inside an object being imaged during a light imaging mode, the light imaging system including an imaging chamber comprising an interior cavity, a camera, and a first sealing member, wherein the object being imaged emits between about $10^3$ and about $10^{10}$ photons/second/centimeter squared/steradian;

a computer tomography imaging system configured to provide three-dimensional spatial information for the internal portion of the object being imaged during an x-ray imaging mode, said computer tomography imaging system including an X-ray producer configured to emit X-rays that pass through the object being imaged and an array of X-ray sensors that receive the X-rays;

a movable stage that supports the object being imaged during and between both the light and x-ray imaging modes such that the multi-modal imaging system images the object in both the light and x-ray imaging modes without substantially disturbing the position of the object during and between imaging modes, the movable stage comprising a second sealing member configured to interface with the first sealing member to provide a substantially light tight seal between the interior cavity of the imaging chamber and a space outside the imaging chamber when the movable stage is within the interior cavity; and at least one processing device in logical communication with both the light imaging system and the computer tomography imaging system, wherein the at least one processing device is configured to construct a three-dimensional representation of a light source distribution within the object by combining the three-dimensional spatial information provided by the computer tomography imaging system with the three-dimensional functional information provided by the light imaging system; and wherein the movable stage is configured to translate the object being imaged along a first direction between the light imaging system and the computer tomography imaging system, and to rotate the object within the light imaging system about an axis parallel to the first direction and to an elongate direction of the object.

2. The multi-modal imaging system of claim 1, wherein the imaging chamber is configured such that the interior cavity is substantially light tight from an ambient space outside the imaging chamber during imaging.

3. The multi-modal imaging system of claim 1, wherein the movable stage remains in a horizontal orientation when the object is being imaged within the imaging chamber.

4. A multi-modal system for imaging an object, comprising:
   an imaging system adapted to image the object in a first imaging mode to capture a first image, the first imaging mode being a computed tomography x-ray mode or other x-ray mode, and to image the object in a second imaging mode different from the first imaging mode to capture a second image, the second imaging mode comprising measuring fluorescence or luminescence from the inside the object, wherein the object being imaged emits between about $10^3$ and about $10^{10}$ photons/second/centimeter squared/steradian;
   a movable stage that supports the object during and between the first and second imaging modes such that the multi-modal imaging system images the object in the first imaging mode and images the object in the second imaging mode without substantially disturbing the position of the object during or between imaging modes, the movable stage comprising a sealing member that interfaces with the imaging system to provide a substantially light tight seal between an interior cavity of the imaging system and a space outside the imaging chamber when the movable stage is within the interior cavity; and
   an electronic processor connected to the imaging system and configured to:
      combine object image information obtained in the first imaging mode and object image information obtained in the second imaging mode; and
      construct a three-dimensional representation of a light source distribution within the object based on the combined information,
   wherein the movable stage is configured to translate the object along a first direction after imaging in the first imaging mode and before imaging in the second imaging mode, and to rotate the object about an axis parallel to the first direction and to an elongate direction of the object during imaging in the second imaging mode.

5. The multi-modal system of claim 4, wherein the imaging system comprises a CCD camera.

6. The multi-modal system of claim 4, wherein the imaging system comprises an array of X-ray sensors.

7. A method of imaging an object, comprising:
   providing a movable stage that supports the object during imaging;
   imaging the object in a first imaging mode to capture a first image, the first imaging mode being a computed tomography x-ray mode or other x-ray mode;
   translating the movable stage with the object thereon along a first direction after the first imaging mode;
   interfacing a sealing member of the movable stage with a sealing member of an imaging chamber to provide a substantially light tight seal between an interior cavity of the imaging chamber and a space outside the imaging chamber;
   imaging the object in the interior cavity in a second imaging mode that uses light from within the object to capture a second image, the second imaging mode being a fluorescence mode or a luminescence mode;
   during the imaging in the second imaging mode, rotating the object about an axis parallel to the first direction and to an elongate direction of the object; and
   combining information from the first image and information from the second image, and constructing a three-dimensional representation of a light source distribution within the object based on the combined information,
   wherein the object being imaged emits between about $10^3$ and about $10^{10}$ photons/second/centimeter squared/steradian; and
   wherein the position of the object on the movable stage is not substantially disturbed during the imaging, translating, and rotating steps.

\* \* \* \* \*